US010935559B2

(12) United States Patent
Chapman et al.

(10) Patent No.: US 10,935,559 B2
(45) Date of Patent: Mar. 2, 2021

(54) METHODOLOGIES AND REAGENTS FOR DETECTING FIBRINOLYSIS AND HYPERFIBRINOLYSIS

(71) Applicants: Haemonetics Corporation, Braintree, MA (US); The Regents of the University of Colorado, a body corporate, Denver, CO (US)

(72) Inventors: Michael P. Chapman, Denver, CO (US); Ernest E. Moore, Denver, CO (US); Katherine M. Norem, Chicago, IL (US)

(73) Assignees: Haemonetics Corporation, Braintree, MA (US); The Regents of the University of Colorado, a body corporate, Denver, CO (US)

(*) Notice: Subject to any disclaimer, the term of this patent is extended or adjusted under 35 U.S.C. 154(b) by 580 days.

(21) Appl. No.: 15/149,868

(22) Filed: May 9, 2016

(65) Prior Publication Data
US 2016/0252534 A1 Sep. 1, 2016

Related U.S. Application Data

(62) Division of application No. 14/270,269, filed on May 5, 2014, now Pat. No. 9,354,243.

(51) Int. Cl.
*G01N 33/86* (2006.01)
*G01N 33/49* (2006.01)
*C12Q 1/56* (2006.01)

(52) U.S. Cl.
CPC ........... *G01N 33/86* (2013.01); *C12Q 1/56* (2013.01); *G01N 33/49* (2013.01)

(58) Field of Classification Search
None
See application file for complete search history.

(56) References Cited

U.S. PATENT DOCUMENTS 5,232,828 A * 8/1993 Phi-Wilson ............ C12N 1/02
422/534
5,290,764 A * 3/1994 Duke, Jr. ............... A61K 38/57
514/13.6

(Continued)

FOREIGN PATENT DOCUMENTS

EP 2 063 273 5/2009 ............ G01N 33/86
WO WO 01/96879 12/2001 ............ G01N 33/86

(Continued)

OTHER PUBLICATIONS

Chapman et al., "Fibrinolysis greater than 3% is the critical value for initiation of antifibrinolytic therapy," J. Trauma Acute Care Surgery, vol. 75, No. 6, pp. 961-967.

(Continued)

*Primary Examiner* — Jill A Warden
*Assistant Examiner* — Brittany I Fisher
(74) *Attorney, Agent, or Firm* — Sunstein Kann Murphy & Timbers LLP

(57) ABSTRACT

In some embodiments, the invention provides a container adapted for detecting hyperfibrinolysis or fibrinolysis in a blood sample using viscoelastic analysis comprising an interior having a coating comprises an inhibitor of fibrinolysis.

11 Claims, 11 Drawing Sheets
(10 of 11 Drawing Sheet(s) Filed in Color)

(56) References Cited

U.S. PATENT DOCUMENTS

| | | | |
|---|---|---|---|
| 6,613,573 B1 | 9/2003 | Cohen | 436/69 |
| 7,422,905 B2 * | 9/2008 | Clague | G01N 11/14 422/430 |
| 7,732,213 B2 | 6/2010 | Cohen et al. | |
| 8,058,023 B2 * | 11/2011 | Gurbel | C12Q 1/56 435/13 |
| 2002/0169408 A1 * | 11/2002 | Beretta | A61B 17/00491 604/19 |
| 2003/0135255 A1 * | 7/2003 | Sundar | A61L 31/10 623/1.11 |
| 2004/0131500 A1 * | 7/2004 | Chow | G01N 11/14 422/72 |
| 2007/0184508 A1 | 8/2007 | Cohen et al. | 435/11 |
| 2007/0207942 A1 * | 9/2007 | Creutz | A61K 8/416 512/2 |
| 2009/0130645 A1 | 5/2009 | Schubert et al. | 435/2 |
| 2010/0228185 A1 * | 9/2010 | Roorda | A61B 17/0057 604/48 |
| 2012/0294767 A1 * | 11/2012 | Viola | G01N 29/024 422/73 |
| 2012/0329082 A1 * | 12/2012 | Viola | B01L 3/5027 435/13 |
| 2013/0029030 A1 * | 1/2013 | Larsen | A61L 15/325 427/2.31 |
| 2013/0102015 A1 | 4/2013 | Schubert | 435/13 |

FOREIGN PATENT DOCUMENTS

| | | | | |
|---|---|---|---|---|
| WO | WO 2005/106467 | 11/2005 | | G01N 33/49 |
| WO | WO/2008/093216 | 8/2008 | | |
| WO | WO 2011/075614 | 6/2011 | | G01N 33/49 |

OTHER PUBLICATIONS

Dirkmann et al., "Factor XIII and Tranexamic Acid But Not Recombinant Factor VIIa Attenuate Tissue Plasminogen Activator-Induced Hyperfibrinolysis in Human Whole Blood," Anesthesia & Analgesia, vol. 114, No. 6, pp. 1182-1188, Jun. 2012.

International Searching Authority, International Search Report and Written Opinion for PCT/US2014/036860, 11 pages, dated Aug. 25, 2014.

U.S. Appl. No. 14/270,269, filed May 5, 2014, now U.S. Publication No. 2015/0316565.

* cited by examiner

METHODOLOGIES AND REAGENTS FOR DETECTING FIBRINOLYSIS AND HYPERFIBRINOLYSIS

CROSS-REFERENCE TO RELATED APPLICATIONS

This application is a divisional application of U.S. patent application Ser. No. 14/270,269 filed May 5, 2014, the entire contents of which is hereby incorporated by reference.

STATEMENT REGARDING FEDERAL SPONSORED RESEARCH OR DEVELOPMENT

This invention was made with government support under Grant No. NIH-T32-GM008315 awarded by the National Institutes of Health. The government has certain rights in the invention.

BACKGROUND ART

The present invention relates to haemostasis.

Haemostasis is a tightly regulated process which causes bleeding to stop. In the body, circulating blood remains fluid under normal conditions, but forms localized clots when the integrity of the vascular system is breeched. Trauma, infection, and inflammation all activate the blood's clotting system, which depends on the interaction of two separate systems: enzymatic proteins in a clotting cascade (e.g., clotting factors such as Factor VII or Factor IX) and activated platelets. The two systems work in concert to plug defects in the broken vessels.

A blood clot (also called a thrombus) that forms during haemostasis is made of two parts—a platelet plug and a mesh of cross-linked fibrin protein. The fibrin results from cleavage of fibrinogen into fibrin by thrombin which is activated during the clotting cascade (see FIG. 1). A blood clot needs to be of sufficient strength to resist dislodgement by circulating blood or mechanical movement. If a particular clotting factor is dysfunctional or absent, as in hemophilia, an insufficient amount of fibrin forms. Similarly, massive consumption of clotting factors in a trauma situation decreases the amount of fibrin formed. Inadequate numbers of platelets resulting from trauma, surgery, or chemotherapy also decrease platelet aggregation, as do genetic disorders, uremia, or salicylate therapy. Ultimately, reduced fibrin formation or platelet aggregation results in clots of inadequate tensile strength. This hypocoagulable state makes the patient prone to bleeding. Conversely, endothelial injury, stasis, cancer, genetic diseases, or other hypercoagulable states lead to thrombosis (i.e., blood clot) formation, exemplified in deep-vein thromboses, pulmonary emboli, and arterial occlusions such as stroke and myocardial infarction.

The precursor of plasmin, plasminogen, is an inactive protein that is incorporated into a blood clot. Tissue plasminogen activator (t-PA) and urokinase are able to convert plasminogen to plasmin, thus activating it and allowing fibrinolysis to occur. Fibrinolysis, the process of breaking down blood clots, so that they do not become problematic, is a normal biological process. Normally, t-PA is released very slowly into the blood by the damaged endothelium of blood vessels. As a result, after bleeding is stopped, the clot is broken down as the inactive plasminogen in the clot is activated to become plasmin, which acts to break down the fibrin mesh holding the clot together. The resulting fragments, called fibrin degradation products (FDPs), are then cleared by other enzymes, or by the kidney and liver.

In some situations, hyperfibrinolysis can also occur. This condition, a form of coagulopathy (bleeding disorder) with markedly enhanced fibrinolytic activity, results in increased and sometimes fatal bleeding.

Hyperfibrinolysis can be acquired or can be congenital. Congenital reasons for hyperfibrinolysis are rare and include deficiency of alpha-2-antiplasmin (alpha-2-plasmin inhibitor) and deficiency in plasminogen activator inhibitor type 1 (PAI-1). The affected individuals show a hemophilia-like bleeding phenotype.

Acquired hyperfibrinolysis can occur in patient with liver disease, patients with severe trauma, patients undergoing major surgical procedures, and patients with other conditions. Indeed, up to 20% of severely injured trauma patients are affected by acquired hyperfibrinolysis, as are other patients with massive hemorrhage.

Known methods to detect fibrinolysis and hyperfibrinolysis include indirect immunochemical methods which detect the elevation of biomarkers such as D-Dimer (cross-linked fibrin degradation products), fibrinogen split products (FSP), complexes of plasmin and alpha-2-antiplasmin (PAP). However, the sensitivity and specificity of these methods is limited because elevation of these biomarkers can also occur induced in other conditions. The classical coagulations tests such as PT (prothrombin time), aPPT (activated partial thromboplastin time) or thrombin time are not very sensitive for fibrinolysis and hyperfibrinolysis, and are influenced by numerous other variables.

Thus, there is a need to for methods to rapidly and accurately diagnose and/or detect fibrinolysis and hyperfibrinolysis.

SUMMARY OF THE EMBODIMENTS

The invention provides methods and reagents to rapidly and accurately detect fibrinolysis and hyperfibrinolysis in a blood sample.

Accordingly, in one aspect, the invention provides a method for detecting fibrinolysis or hyperfibrinolysis in a blood sample. The method includes subjecting a first portion of a blood sample comprising reduced platelet function to viscoelastic analysis in the absence of an inhibitor of fibrinolysis to obtain the coagulation characteristic of the first portion at the time point; and subjecting a second portion of the blood sample comprising reduced platelet function to viscoelastic analysis in the presence of an inhibitor of fibrinolysis to obtain a coagulation characteristic of the second portion at a time point; wherein a difference between the coagulation characteristic of the first portion and the coagulation characteristic of the second portion indicates fibrinolysis or hyperfibrinolysis in the blood sample. In some embodiments, blood sample (e.g., prior to reduction of platelet function in the blood sample) is taken from a source. In some embodiments, the source is a blood donation vehicle (e.g., a bag or tube). In some embodiments, the source is a patient is human. In some embodiments, the patient from whom the blood sample is taken is responsive to the inhibitor of fibrinolysis used in the method.

In some embodiments, the coagulation characteristic is an amplitude of an output of the viscoelastic analysis. In some embodiments, the coagulation characteristic a first derivative an amplitude of an output of the viscoelastic analysis. In some embodiments, the time point is at a time of maximum clot strength of the first portion. In some embodiments, the time point is between about 15 to about 35 minutes after the viscoelastic analysis is started or is less than 20 minutes after the viscoelastic analysis is started. In some embodiments, the time point is obtained is at a time that clot firmness reaches 20 mm in the blood sample not treated with the inhibitor of fibrinolysis.

In various embodiments, the difference between the coagulation characteristic of the first portion and the coagulation characteristic of the second portion that is at least 1% indicates fibrinolysis or hyperfibrinolysis in the blood sample. In further embodiments, the difference between the coagulation characteristic of the first portion and the coagulation characteristic of the second portion that is at least 2% indicates fibrinolysis or hyperfibrinolysis in the blood sample.

In some embodiments, the blood sample comprising reduced platelet function comprises an inhibitor of platelet function. In some embodiments, the inhibitor of platelet function is a glycoprotein IIb/IIIa receptor inhibitor, such as abciximab, eptifibatide, or tirofiban. In some embodiments, the inhibitor of platelet function is an adenosine diphosphate (ADP) receptor inhibitor, an adenosine reuptake inhibitor, or a thromboxane inhibitor. In some embodiments, the inhibitor of platelet function is cytochalasin D. In some embodiments, the inhibitor of platelet function is a combination of different inhibitors (e.g., a combination of abciximab, eptifibatide, tirofiban, an adenosine diphosphate (ADP) receptor inhibitor, an adenosine reuptake inhibitor, a thromboxane inhibitor and/or cytochalasin D.

In some embodiments, the blood sample comprising reduced platelet function is a platelet-reduced blood sample. For example, the platelet-reduced blood sample may be obtained by physical removal of the platelets from the blood sample.

In some embodiments, the inhibitor of fibrinolysis is tranexamic acid. In some embodiments, the inhibitor of fibrinolysis is aminocaproic acid, ε-aminocaproic acid, or aprotinin. In some embodiments, the inhibitor of fibrinolysis is a combination of aminocaproic acid, ε-aminocaproic acid, tranexamic acid, and/or aprotinin.

In some embodiments the sample is excited at a resonant frequency and its behavior may be observed by an electromagnetic or light source as coagulation occurs. In other embodiments the sample's characteristics may be observed for changes with a light source without exciting the sample.

In some embodiments, the viscoelastic analysis is performed using a hemostasis analyzer. The hemostasis analyzer may be a TEG thromboelastography analyzer system or in a ROTEM thromboelastometry analyzer system. In some embodiments, the viscoelastic analysis is performed using a container containing the sample on an interior of the container and a pin, wherein the pin moves relative to the container. In some embodiments, the viscoelastic analysis is performed using a container containing the sample on an interior of the container and a pin, wherein the container moves relative to the pin. In some embodiments the sample is excited at a resonant frequency and its behavior may be observed by an electromagnetic or light source as coagulation occurs. In other embodiments the sample's characteristics may be observed for changes with a light source without exciting the sample.

In some embodiments, the inhibitor of fibrinolysis is included in a coating on the interior of the container. In some embodiments, the inhibitor of fibrinolysis is added to the sample in the container. In some embodiments, the inhibitor of platelet function is included in a coating on the interior of the container. In some embodiments, the inhibitor of platelet function is added to the sample in the container.

In another aspect, the invention provides a method for identifying an inhibitor of fibrinolysis that will achieve a beneficial response in a patient undergoing or likely to undergo fibrinolysis or hyperfibrinolysis, comprising: subjecting a first portion of a blood sample comprising reduced platelet function to viscoelastic analysis in the absence of an inhibitor of fibrinolysis to obtain the coagulation characteristic of the first portion at the time point; subjecting a second portion of the blood sample comprising reduced platelet function to viscoelastic analysis in the presence of first inhibitor of fibrinolysis to obtain a coagulation characteristic of the second portion at a time point; subjecting a third portion of a blood sample comprising reduced platelet function to viscoelastic analysis in the presence of first inhibitor of fibrinolysis to obtain a coagulation characteristic of the third portion at a time point; and comparing a first difference between the coagulation characteristic of the first portion and the coagulation characteristic of the second portion in the presence of the first inhibitor, and a second difference between the coagulation characteristic of the first portion and the coagulation characteristic of the third portion in the presence of the second inhibitor, wherein the patient will have beneficial result from treatment with the first inhibitor if the first difference is greater than the second difference, and the patient will have a beneficial result from treatment with the second inhibitor if the second inhibitor is greater than the first inhibitor.

In some embodiments, the patient is human.

In some embodiments, the first inhibitor of fibrinolysis is tranexamic acid. In some embodiments, each of the first inhibitor and the second inhibitor of fibrinolysis is selected from the group consisting of ε-aminocaproic acid, tranexamic acid, aminocaproic acid and aprotinin, wherein the first inhibitor and the second inhibitor are not the same.

In a further aspect, the invention provides a container adapted for detecting hyperfibrinolysis or fibrinolysis in a blood sample using viscoelastic analysis comprising an interior having a coating comprises an inhibitor of fibrinolysis. In some embodiments, the inhibitor of fibrinolysis is tranexamic acid. In some embodiments, the inhibitor of fibrinolysis is aminocaproic acid, ε-aminocaproic acid, or aprotinin. In some embodiments, the inhibitor of fibrinolysis is a combination of aminocaproic acid, ε-aminocaproic acid, tranexamic acid, and/or aprotinin.

In some embodiments, the viscoelastic analysis is performed using a TEG thromboelastography analyzer system or in a ROTEM thromboelastometry analyzer system. In some embodiments, the inhibitor of fibrinolysis is formulated with sugar in the coating. In some embodiments, the inhibitor is formulated with sodium azide in the coating.

In some embodiments, the coating further comprises an inhibitor of platelet function. In some embodiments, the inhibitor of platelet function is a glycoprotein IIb/IIIa receptor inhibitor, such as abciximab, eptifibatide, or tirofiban. In some embodiments, the inhibitor of platelet function is an adenosine diphosphate (ADP) receptor inhibitor, adenosine reuptake inhibitor, or a thromboxane inhibitor. In some embodiments, the inhibitor of platelet function is cytochalasin D. In some embodiments, the inhibitor of platelet function is a combination of different inhibitors (e.g., a combination of abciximab, eptifibatide, tirofiban, an adenosine diphosphate (ADP) receptor inhibitor, an adenosine reuptake inhibitor, a thromboxane inhibitor and/or cytochalasin D.

In some embodiments, the container is located on a cassette or plate, wherein the cassette or plate further comprises a second container.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which.

DETAILED DESCRIPTION OF SPECIFIC EMBODIMENTS

Figure 1:
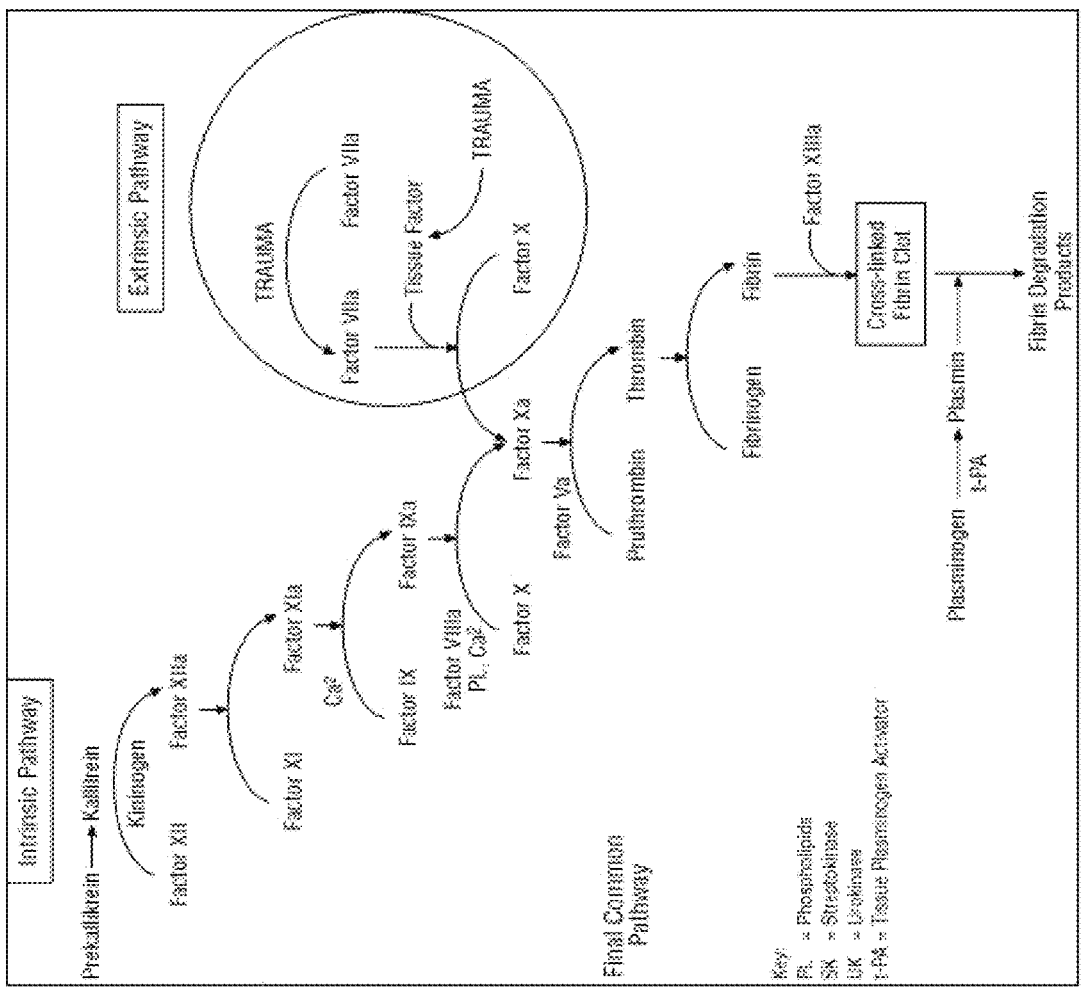
FIG. 1 is a schematic diagram showing the clotting cascade that leads eventually to the formation of the fibrin clot made of cross-linked fibrin. Activation of plasminogen by t-PA produces plasmin which degrades the fibrin into fibrin degradation products.

In some embodiments, the invention provides methods and reagents (e.g., cups) for detecting fibrinolysis and hyperfibrinolysis. The invention stems, in part, from the unexpected discovery that platelet participation in the clot can partially mask the onset and extent of fibrinolysis. Therefore, reducing platelet function in a blood sample being tested for its hemostasis status can speed the detection of fibrinolysis and hyperfibrinolysis in the blood sample (and in the patient from whom the blood sample was taken).

The publications (including patent publications), web sites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

As used herein, the term 'haemostasis" (or "hemostasis") is meant a process which causes bleeding to stop by the blood coagulating, and also the process by which the coagulated blood (or blood clot) dissolves. The term includes blood coagulation by formation of a fibrin-containing blood clot, and the breakdown of that clot by activation of plasmin to dissolve the fibrin mesh holding the clot together.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. Thus, to be complete, it is necessary to measure continuously all phases of patient hemostasis as a net product of whole blood components in a non-isolated, or static fashion. To give an example of the consequences of the measuring of an isolated part of hemostasis, assume that a patient developed fibrinolysis, which is caused by the activation of plasminogen into plasmin, an enzyme that breaks down the clot. In this scenario, a byproduct of this process of fibrinogen degrading product (FDP), which behaves as an anticoagulant. If the patient is tested only for anticoagulation and is treated accordingly, this patient may remain at risk due to not being treated with antifibrinolytic agents (e.g., treated with tranexamic acid).

The detection of fibrinolysis or hyperfibrinolysis is difficult. Moreover, to be beneficial to a patient who is may need to be treated with an antifibrinolytic agent (e.g., during surgery or trauma), the detection of fibrinolysis or hyperfibrinolysis is preferably very rapid. In some embodiments, the invention provides methods and reagents for rapidly detecting fibrinolysis or hyperfibrinolysis in a blood sample.

Accordingly, in a first aspect, the invention provides method for detecting fibrinolysis or hyperfibrinolysis in a blood sample, comprising obtaining a blood sample, where the blood sample has a reduced platelet function; subjecting a first portion of the blood sample to viscoelastic analysis in the presence of an inhibitor of fibrinolysis to obtain a coagulation characteristic of the first portion at a time point; and subjecting a second portion of the blood sample to viscoelastic analysis in the absence of an inhibitor of fibrinolysis to obtain the coagulation characteristic of the second at the time point; wherein the difference between the coagulation characteristic of the first portion and the coagulation characteristic of the second portion indicates fibrinolysis or hyperfibrinolysis in the blood sample.

In some embodiments, the blood sample (e.g., prior to the reduction of platelet function in the blood sample) is taken from a source. The source can be any source including a donor bag or directly from a patient. In some embodiments, the patient from whom the blood sample is taken is responsive to the inhibitor of fibrinolysis used in the method.

As used herein, the term "fibrinolysis" means the breakdown of a blood clot due to the conversion of inactive plasminogen in the clot to active plasmin. During fibrinolysis, active plasmin breaks down the fibrin mesh holding the clot together (see FIG. 1).

By "hyperfibrinolysis" is meant a form of coagulopathy (bleeding disorder) with markedly enhanced fibrinolytic activity, results in increased and sometimes fatal bleeding. Hyperfibrinolysis can be acquired or can be congenital. Congenital hyperfibrinolysis can be due to deficiency of alpha-2-antiplasmin (alpha-2-plasmin inhibitor) and deficiency in plasminogen activator inhibitor type 1 (PAI-1). Acquired hyperfibrinolysis can occur in patient with liver disease, patients with severe trauma, patients undergoing major surgical procedures, and patients with other conditions. Indeed, up to 20% of severely injured trauma patients are affected by acquired hyperfibrinolysis, as are other patients with massive hemorrhage.

As used herein, by "blood sample" is meant a sample of blood taken, for example, from a patient. The patient may be a human, but may also be any other animal (e.g., veterinary animal or exotic animal). Blood is the circulating tissue of an organism that carries oxygen and nutritive materials to the tissues and removes carbon dioxide and various metabolic products for excretion. Blood consists of a pale yellow or gray yellow fluid, plasma, in which are suspended red blood cells, white blood cells, and platelets.

In some embodiments, the blood sample is whole blood. The blood may be untreated, or may be citrate blood (e.g., whole blood collected into a 3.5 mL container containing 3.2% citrate).

By "viscoelastic analysis" is meant any analysis method that measures the characteristics of elastic solid (e.g., fibrin solids) and fluids. In other words, viscoelastic analysis allows the study of properties of a viscous fluid, such as blood or a blood sample. In some embodiments, the viscoelastic analysis is performed under conditions that mimic the conditions in vivo that result in haemostasis. For example, the condition may include a temperature that mimics a body temperature (e.g., a temperature of 37° C.). The condition may also include clot formation and dissolution at flow rates that mimic those found in blood vessels.

In some embodiments, viscoelastic analysis of a blood sample may include subjecting the blood sample to analysis on a hemostasis analyzer instrument. One non-limiting viscoelastic analysis method is the thromboelastography ("TEG") assay. Thus in some embodiments, the viscoelastic analysis includes subjecting a blood sample to analysis using thromboelastography (TEG), which was first described by Helmut Hartert in Germany in the 1940's.

Various devices that perform thromboestography, and methods for using it are described in U.S. Pat. Nos. 5,223,227; 6,225,126; 6,537,819; 7,182,913; 6,613,573; 6,787,363; 7,179,652; 7,732,213; 8,008,086; 7,754,489; 7,939,329; 8,076,144; 6,797,419; 6,890,299; 7,524,670; 7,811,792; 20070092405; 20070059840; 8,421,458; US 20120301967; and U.S. Pat. No. 7,261,861, the entire disclosures of each of which are hereby expressly incorporated herein by reference.

Thromboelastography (TE) monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood. In essence, the clot is the elementary machine of hemostasis. Haemostasis instruments that measure haemostasis are able to measure the ability of the clot to perform mechanical work throughout its structural development. These haemostasis analyzers measure continuously all phases of patient hemostasis as a net product of whole blood components in a non-isolated, or static fashion from the time of test initiation until initial fibrin formation, through clot rate strengthening and ultimately clot strength through clot lysis.

In some embodiments, the viscoelastic analysis and/or the haemostasis analyzer comprises a container which is in contact with the blood.

As used herein, by "container" is meant a rigid surface (e.g., a solid surface), a portion of which contacts a portion of a blood sample placed into the container at any point during the viscoelastic analysis. The portion of the container that contact the portion of blood sample may also be referred to as the "interior" of the container. Note that the phase "into the container" does not mean that the container has a bottom surface which is in contact with the portion of the blood sample. Rather, the container can be a ring-shaped structure, where the inside of the ring is the interior of the container, meaning that the inside of the ring is the portion of the ring-shaped container that contacts a portion of the blood sample. A blood sample can flow into the container and be held there, for example, by vacuum pressure or surface tension.

Still additional types of containers that are included in this definition are those present on plates and cassettes (e.g., a microfluidic cassette), where the plate or cassette has multiple channels, reservoirs, tunnels, and rings therein. Each of the contiguous channels (comprising, for example, a channel, a reservoir, and a ring) is a container, as the term is used herein. Hence, there may be multiple containers on one cassette. U.S. Pat. No. 7,261,861 (incorporated herein by reference) describes such a cassette with multiple channels or containers. Any of the surfaces in any of the channels or tunnels of the cassette may be an interior of the container if that surface comes into contact with any portion of the blood sample, at any time during the viscoelastic analysis.

One non-limiting haemostasis analyzer instrument is described in U.S. Pat. No. 7,261,861; US Patent Publication No. US US20070092405; and US Patent Publication No. US20070059840.

Another non-limiting haemostasis analyzer instrument that performs viscoelastic analysis using thromboelastography is the TEG thromboelastograph hemostasis analyzer system sold commercially by Haemonetics, Corp. (Braintree, Mass.).

Thus, the TEG assay may be performed using the TEG thromboelastograph hemostasis analyzer system that measures the mechanical strength of an evolving blood cloth. To run the assay, the blood sample is placed into a container (e.g., a cup or a cuvette), and a metal pin goes into the center of the container. Contact with the interior walls of the container (or addition of a clot activator to the container) initiates clot formation. The TEG thromboelastograph hemostasis analyzer then rotates the container in an oscillating fashion, approximately 4.45 degrees to 4.75 degrees, every 10 seconds, to imitate sluggish venous flow and activate coagulation. As fibrin and platelet aggregates form, they connect the inside of the container with the metal pin, transferring the energy used to move the container in the pin. A torsion wire connected to the pin measures the strength of the clot over time, with the magnitude of the output directly proportional to the strength of the clot. As the strength of the clot increases over time, a classic TEG tracing curve develops (See FIG. 2).

Figure 2:
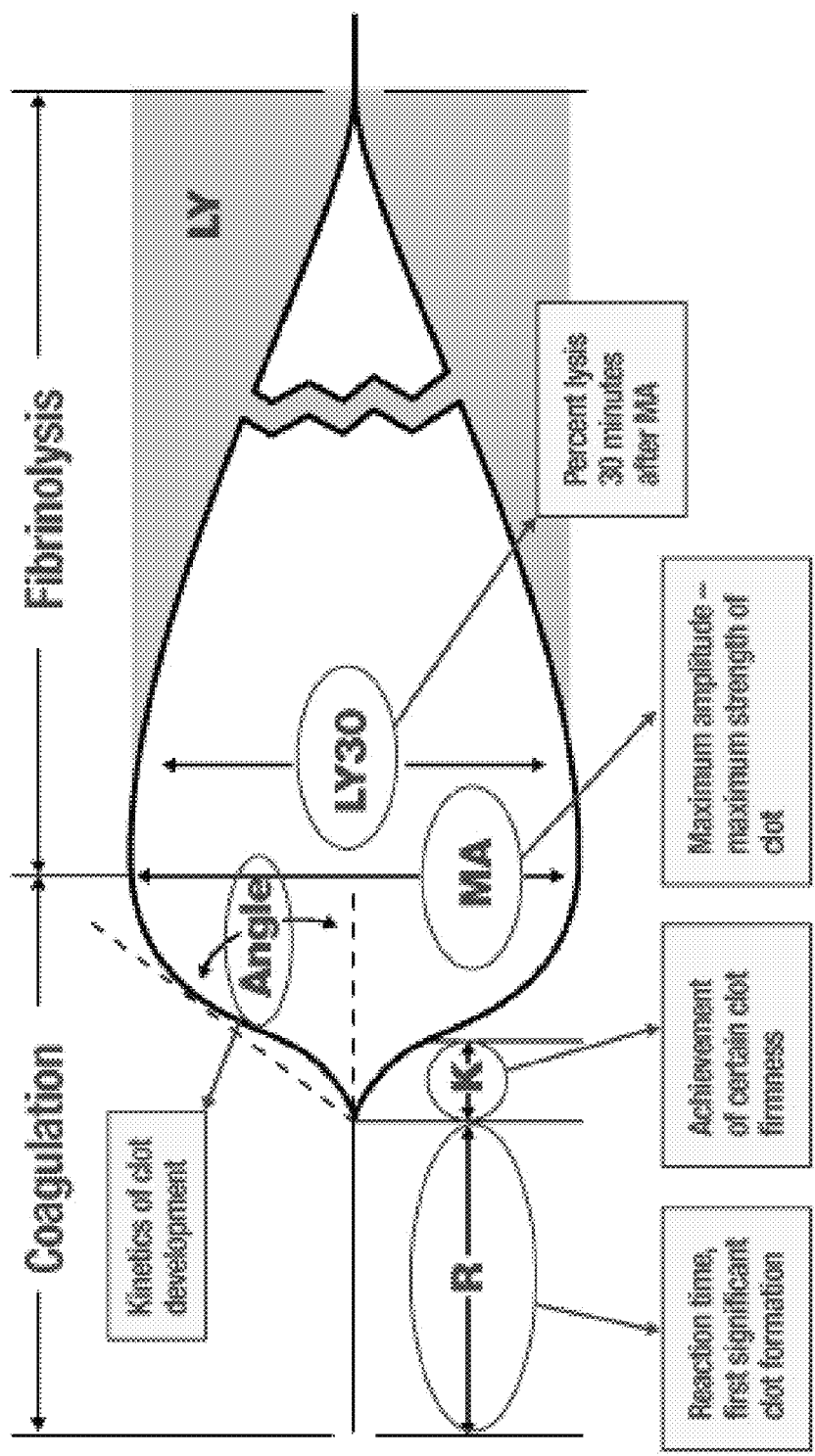
FIG. 2 is schematic diagram showing a TEG tracing from a sample with normal haemostasis; that is, a normal amount of fibrinolysis and no hyperfibrinolysis. The R (reaction time) is the time of formation of the fibrin strand polymers, K (clot kinetics, measured in minutes) is the speed at which the clot forms, α is the slope drawn from R to K, and MA (maximum amplitude, measured in mm) is the strength of the clot. The LY30 is the percent lysis present thirty minutes after the MA.

The rotational movement of the pin is converted by a transducer to an electrical signal, which can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art. As shown in FIG. 2, the resulting hemostasis profile (i.e., a TEG tracing curve) is a measure of the time it takes for the first fibrin strand to be formed, the kinetics of clot formation, the strength of the clot (measured in millimeters (mm) and converted to shear elasticity units of dyn/cm2) and dissolution of clot. See also Donahue et al., *J. Veterinary Emergency and Critical Care:* 15(1): 9-16. (March 2005), herein incorporated by reference The descriptions for several of these measured parameters are as follows:

R is the time is the period of time of latency from the time that the blood was placed in the TEG 5000 analyzer until the initial fibrin formation. This is typically takes about 30 second to about 10 minutes. For patients in a hypocoagulable state (i.e., a state of decreased coagulability of blood), the R number is longer, while in a hypercoagulable state (i.e., a state of increased coagulability of blood), the R number is shorter.

K value (measured in minutes) is the time from the end of R until the clot reaches 20 mm and this represents the speed of clot formation. This K value is about 0 to about 4 minutes (i.e., after the end of R). In a hypocoagulable state, the K number is longer, while in a hypercoagulable state, the K number is shorter.

α measures the rapidity of fibrin build-up and cross-linking (clot strengthening) It is angle between the line formed from the split point tangent to the curve and the horizontal axis. This angle is typically about 47° to 74°. In a hypocoagulable state, the a degree is lower, while in a hypercoagulable state, the α degree is higher.

MA or Maximum Amplitude in mm, is a direct function of the maximum dynamic properties of fibrin and platelet bonding and represents the ultimate strength of the fibrin clot. This number is typically from about 54 mm to about 72 mm, and the MA occurs typically between about 15 to about 35 minutes after the start of the viscoelastic assay. Note that if the blood sample tested has a reduced platelet function, this MA represents the strength of the clot based on fibrin only. Decreases in MA may reflect a hypocoagulable state (e.g., with platelet dysfunction or thrombocytopenia), whereas an increased MA (e.g., coupled with decreased R) may be suggestive of a hypercoagulable state LY30 measures the rate of amplitude reduction 30 minutes after MA and represents clot retraction, or lysis. The LY30 is thus a percentage decrease in amplitude 30 minutes after the MA. This number is typically 0% to about 8%. In some embodiments, a hypocoagulable state is present if the LY30 is greater than 7.5%. However, recent findings have shown that this percentage may be too high to identify a hypocoagulable state in a patient. Accordingly, in some embodiments, an LY30 that is greater than 6%, or greater than about 5%, or greater than about 4%, or greater than about 3.5%, or greater than about 3% identifies a patient with a hypocoagulable state.

If fibrinolysis occurs, fibrinolysis or dissolution of the clot decreases the strength of the clot, causing the maximum amplitude (MA) of the TEG tracing to decrease, causing the LY30 percentage to rise (see FIG. 2).

Another viscoelastic hemostasis assay that can be used is the thromboelastometry ("TEM") assay. This TEM assay may be performed using the ROTEM Thromboelastometry Coagulation Analyzer (TEM International GmbH, Munich, Germany), the use of which is well known (See, e.g., Sorensen, B., et al., *J. Thromb. Haemost.*, 2003. 1(3): p. 551-8. Ingerslev, J., et al., *Haemophilia*, 2003. 9(4): p. 348-52. Fenger-Eriksen, C., et al. *Br J Anaesth*, 2005. 94(3): p. 324-9]. In the ROTEM analyzer, the blood sample is placed into a container (also called a cuvette or cup) and a cylindrical pin is immersed. Between pin and the interior wall of the container there is a gap of 1 mm which is bridged by the blood. The pin is rotated by a spring to the right and the left. As long as the blood is liquid (i.e., unclotted), the movement is unrestricted. However, when the blood starts clotting, the clot increasingly restricts the rotation of the pin with rising clot firmness. The pin is connected to an optical detector. This kinetic is detected mechanically and calculated by an integrated computer to the typical tracing curves (TEMogram) and numerical parameters (see FIGS. 3A and 3B).

Figure 3A:
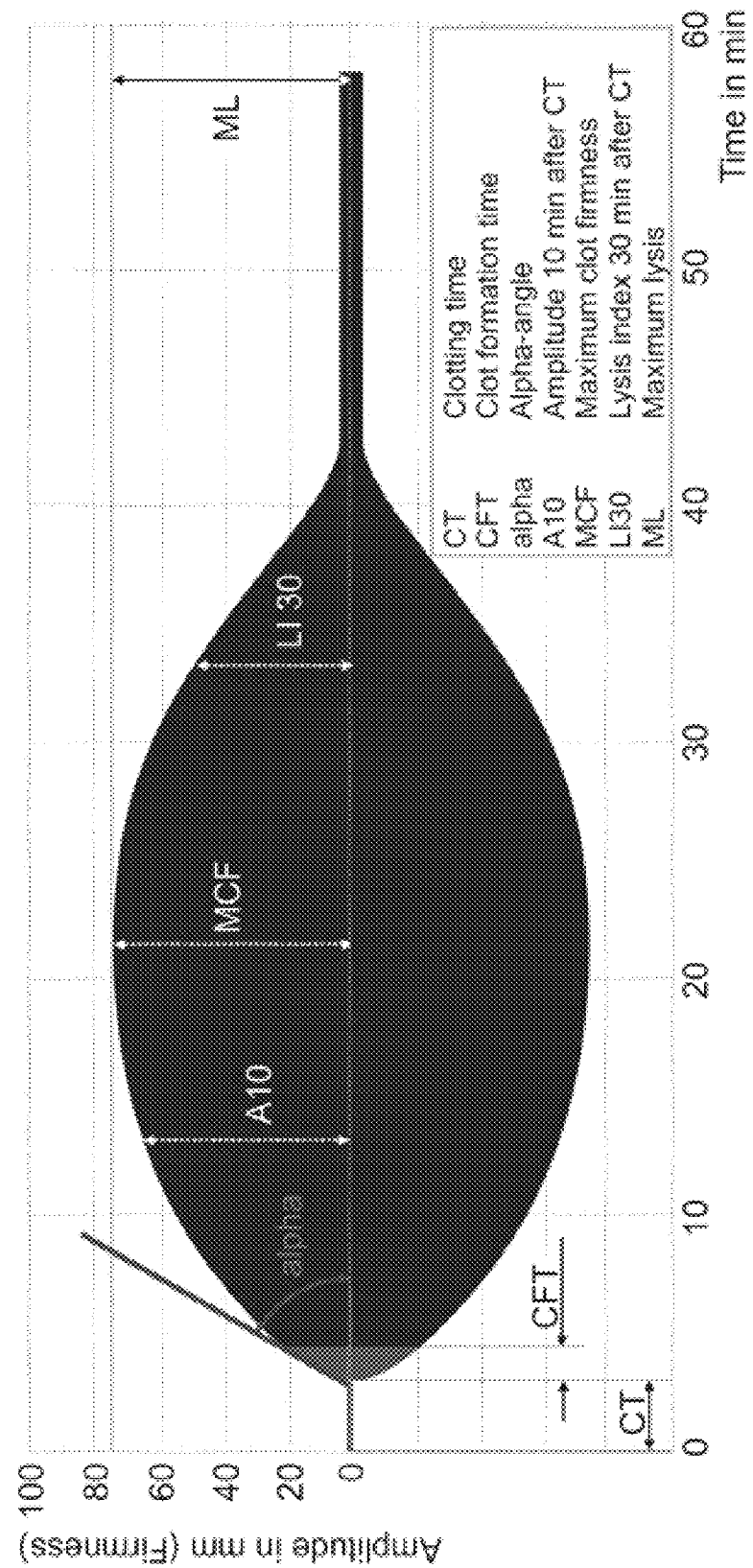
FIG. 3A is schematic diagram showing a TEMogram tracing. CT indicates clotting time, CFT indicates clot formation time, alpha is the alpha-angle, lambda-angle is the lysis rate, MCF is the maximum clot firmness, LI130 is the lysis index 30 minutes after CT, and ML is maximum lysis.
Figure 3B:
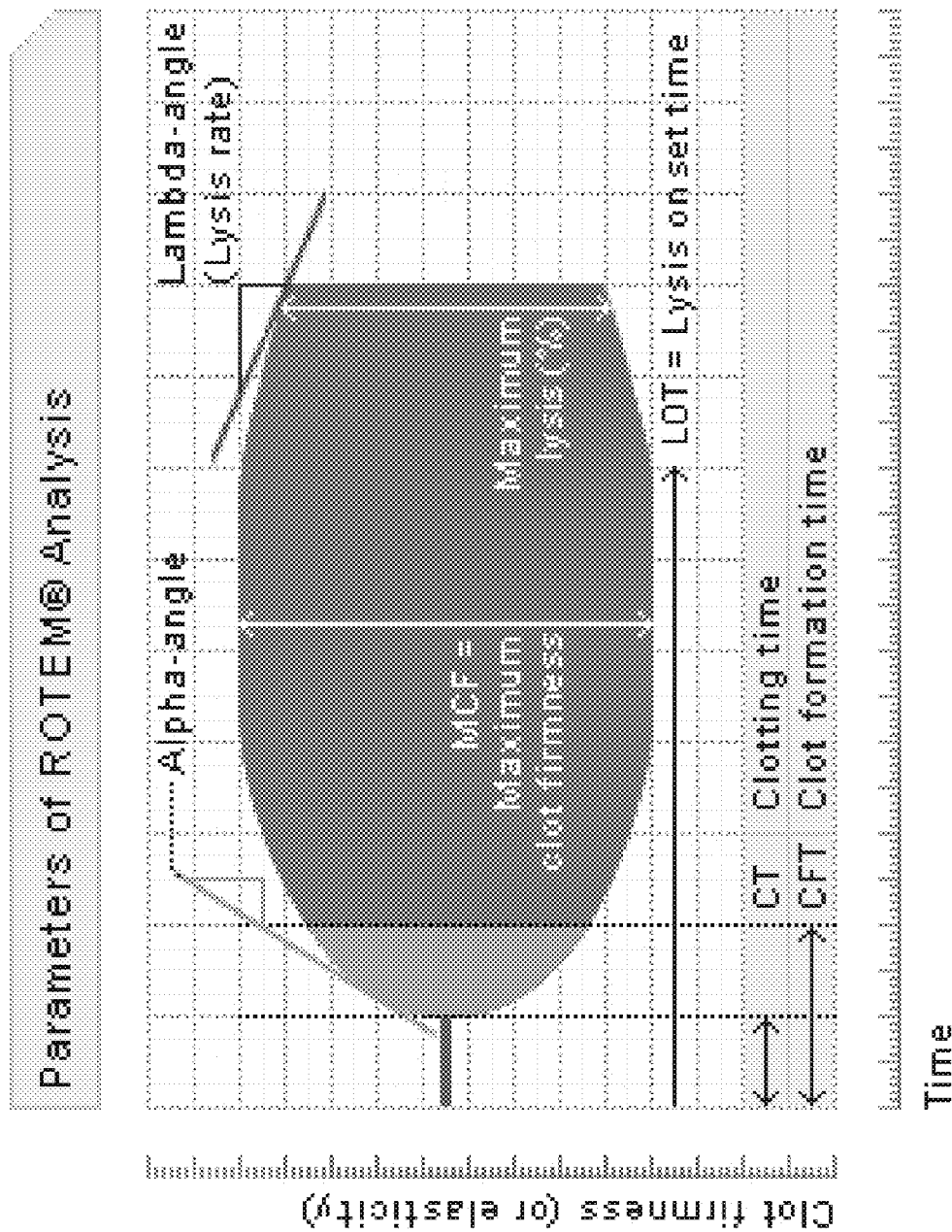
FIG. 3B is schematic diagram showing another TEMogram tracing.

In the ROTEM Thromboelastometry Coagulation Analyzer, the movement of the pin can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile (called a TEMogram. Such a configuration of the computer is well within the skills of one having ordinary skill in the art. As shown in FIGS. 3A and 3B, the resulting hemostasis profile (i.e., a TEM tracing curve) is a measure of the time it takes for the first fibrin strand to be formed, the kinetics of clot formation, the strength of the clot (measured in millimeters (mm) and converted to shear elasticity units of dyn/cm2) and dissolution of clot. The descriptions for several of these measured parameters are as follows:

CT (clotting time) is the period of time of latency from the time that the blood was placed in the ROME analyzer until the clot begins to form.

CFT (Clot formation time): the time from CT until a clot firmness of 20 mm point has been reached.

alpha-angle: The alpha angle is the angle of tangent between 2 and the curve

MA or Maximum Amplitude in mm, is a direct function of the maximum dynamic properties of fibrin and platelet bonding and represents the ultimate strength of the fibrin clot. If the blood sample tested has a reduced platelet function, this MA is a direct function of the fibrin bonding only.

MCF (Maximum clot firmness): MCF is the greatest vertical amplitude of the trace. MCF reflects the absolute strength of the fibrin and platelet clot.

A10 (or A5, A15 or A20 value). This value describes the clot firmness (or amplitude) obtained after 10 (or 5 or 15 or 20) minutes and provide a forecast on the expected MCF value at an early stage.

LI30 (Lysis Index after 30 minutes). The LI30 value is the percentage of remaining clot stability in relation to the MCF value at 30 min after CT.

ML (Maximum Lysis). The ML parameter describes the percentage of lost clot stability (relative to MCF, in %) viewed at any selected time point or when the test has been stopped.

A low LI30 value or a high ML value indicates hyperfibrinolysis. While in normal blood fibrinolysis activity is quite low, in clinical samples a more rapid loss of clot stability by hyperfibrinolysis may lead to bleeding complications which can be treated by the administration of antifibrinolytic drugs.

Thus, parameters of interest in TEG or TEM assays include the maximum strength of the clot which is a reflection of clot strength. This is the MA value in the TEG assay, and the MCF value in the TEM assay. The reaction time (R) in TEG (measured in sec) and clotting time (CT) in TEG is the time until there is first evidence of clot; clot kinetics (K, measured in minutes) is a parameter in the TEG test indicating the achievement of clot firmness; and α in TEG or alpha-angle in TEM is an angular measurement from a tangent line drawn to the curve of the TEG tracing or TEM tracing starting from the point of clot reaction time that is reflective of the kinetics of clot development. (See Trapani, L. M. Thromboelastography: Current Applications, Future Directions", Open Journal of Anesthesiology 3(1): Article ID: 27628, 5 pages (2013); and Kroll, M. H., "Thromboelastography: Theory and Practice in Measuring Hemostasis," *Clinical Laboratory News: Thromboelastography* 36(12), December 2010; instruction manuals for the TEG instrument (available from Haemonetics, Corp.), and the instruction manual for the ROTEM instrument (available from TEM International GmbH), all of which documents are herein incorporated by reference in their entireties.

In some embodiments, the parameters (and hence the coagulation characteristics) are recorded by observation of different excitation levels of the sample as coagulation occurs. For example, where the container is a microfluidic cassette, or a particular channel in the cassette, the blood sample may be excited at a resonant frequency and its behavior observed by an electromagnetic or light source as coagulation occurs. In other embodiments the sample's coagulation characteristics may be observed for changes with a light source without exciting the sample.

Because a single cassette may have multiple containers (e.g., different channels in the cassette), the sample in a container contacted with an inhibitor of fibrinolysis is easily directly comparable to a sample in a container (e.g., in an adjacent channel in the same microfluidic cassette) that is not contacted with the inhibitor of fibrinolysis.

Figure 4:
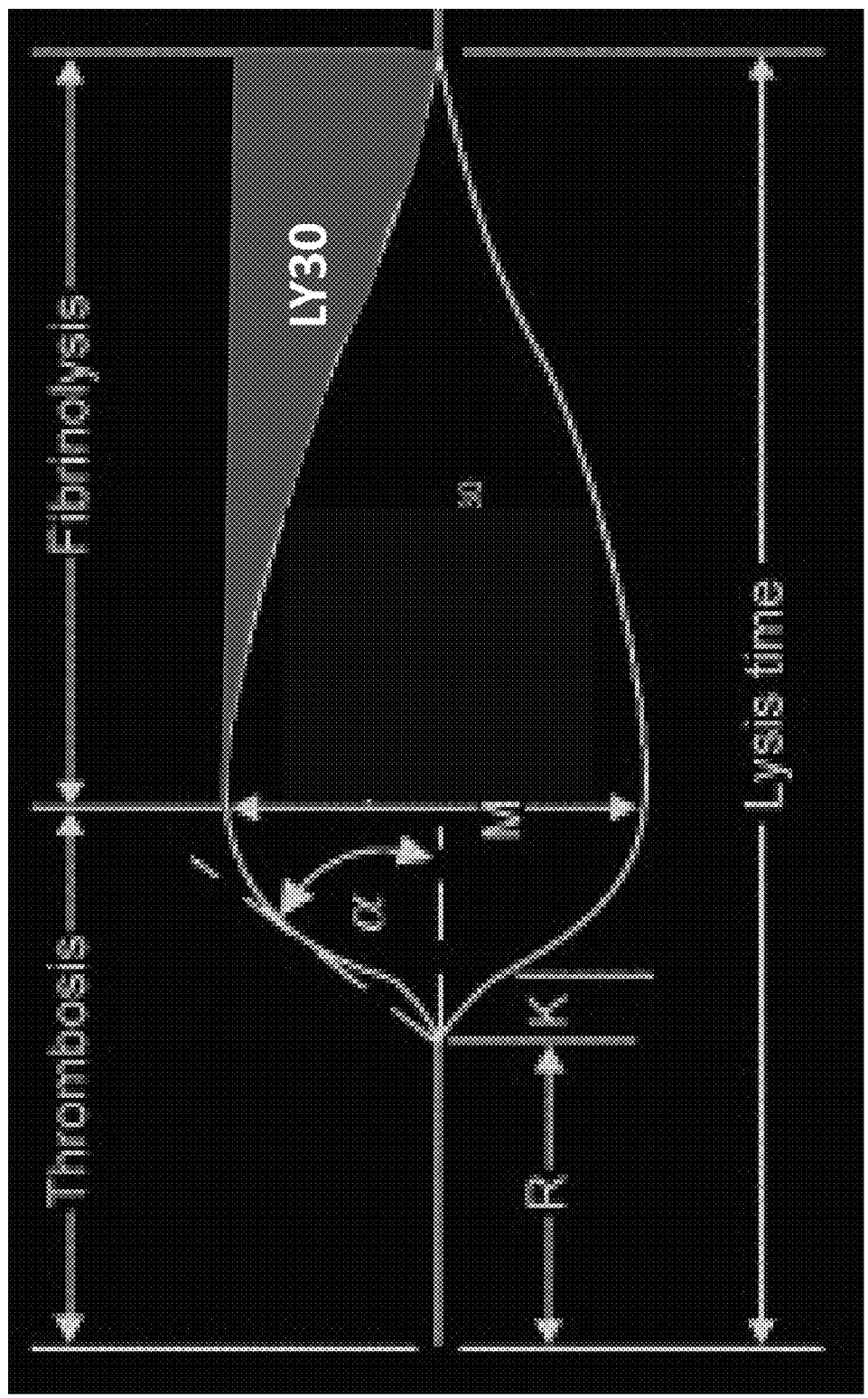
FIG. 4 is a schematic diagram showing a TEG tracing showing calculation of the LY30 measurement.

When no fibrinolysis occurs, the amplitude value at the MA on a TEG tracing and the amplitude value at the MCF on a TEM tracing stays constant or may decrease slightly due to clot retraction. However, as fibrinolysis occurs (e.g., in a hypocoagulable state), the curve of the TEG tracing and the TEM tracing starts to decay. The resultant loss in potential area-under-the-curve in the 30 minutes following Maximum Amplitude in the TEG assay is called the LY30 (see FIG. 4). LY30, the percentage of lysis 30 minutes after the maximum amplitude point (expressed as a percentage of the clot lysed) and clot firmness (G, measured in dynes/cm$^2$), indicates the rate of clot lysis. The corresponding value in the TEM assay is the LI30 value (see FIG. 3A)

This LY30 is the usual metric of fibrinolysis. However, this parameter has some limitations including lack of sensitivity and specificity. Most importantly, the LY30 parameter takes at least 30 minutes to obtain. In normal patients, obtaining the LY30 in at least thirty minutes (because the 30 minutes must be added to whatever the time it took the clot to form in the first place) is adequate. However, in some occasions (e.g., in patients undergoing trauma, hemorrhaging, or during surgery), waiting the at least 30 minutes to determine if the patient's blood is clotting normally may be detrimental to the patient's health. For these patients with a high LY30 who are in a hypocoagulable state, the sooner the patient can be treated with a fibrinolysis inhibitor (e.g., tranexamic acid or aprotinin).

As used herein, by a "coagulation characteristic" is meant a parameter that indicates the haemostasis status of the blood sample being tested. For example, the coagulation characteristic may be the amplitude of the output of the viscoelastic analysis with respect to a time point. Note that the time at which the coagulation characteristic is taken need not be the MA of the sample not treated with the inhibitor of fibrinolysis. The time point can be any time point, so long as the time point is the same. For example, the time point may be between about 15 to about 35 minutes after the start of the viscoelastic analysis assay. The time point may also be the moment when the TEG tracing of the inhibitor of fibrinolysis-treated sample starts to diverge from the TEG tracing of the sample not treated with the inhibitor of fibrinolysis. Thus, the time point may be as early as about 2 minutes or about 5 minutes after the viscoelastic analysis is started.

Other coagulation characteristics measured using a viscoelastic analysis assay can be used in a similar manner to determine if a patient has fibrinolysis or hyperfibrinolysis. For example, in the TEG assay, any of R (reaction time), K (time clot firmness is achieved), a (kinetics of clot development), MA (maximum amplitude), and LY30 can be compared (see FIGS. 2 and 4). For the TEM assay, any of CT (clotting time), CFT (clot formation time), alpha angle, MCF (maximum clot firmness), A10 (amplitude 10 minutes after CT), LI30 (lysis index 30 minutes after CT) and ML (maximum lysis) can be compared (see FIGS. 3A-3B) as well as derivatives of any and all of these parameters can also be used as coagulation characteristics.

In some embodiments, the derivative of the viscoelastic read-out from the blood sample (e.g., a sample that is platelet function-reduced) that is not treated with an antifibrinolytic agent is compared to the derivative of the viscoelastic read-out from the blood sample that is treated with the antifibrinolytic agent. For historic reasons, the parameters of a TEG or a TEM tracing shows the amplitude (in mm) on the y axis and the time on the x axis. The first derivative of a TEG or a TEM tracing is, therefore, velocity (i.e., the slope of the tracing line). The velocity of a tracing from a blood sample not treated with an antifibrinolytic agent can thus be compared to the velocity of the viscoelastic read-out from the blood sample that is treated with the antifibrinolytic agent. This value is called the ΔVA. When there is a difference in the ΔVA, that difference identifies fibrinolysis or hyperfibrinolysis in the sample.

Figure 6:
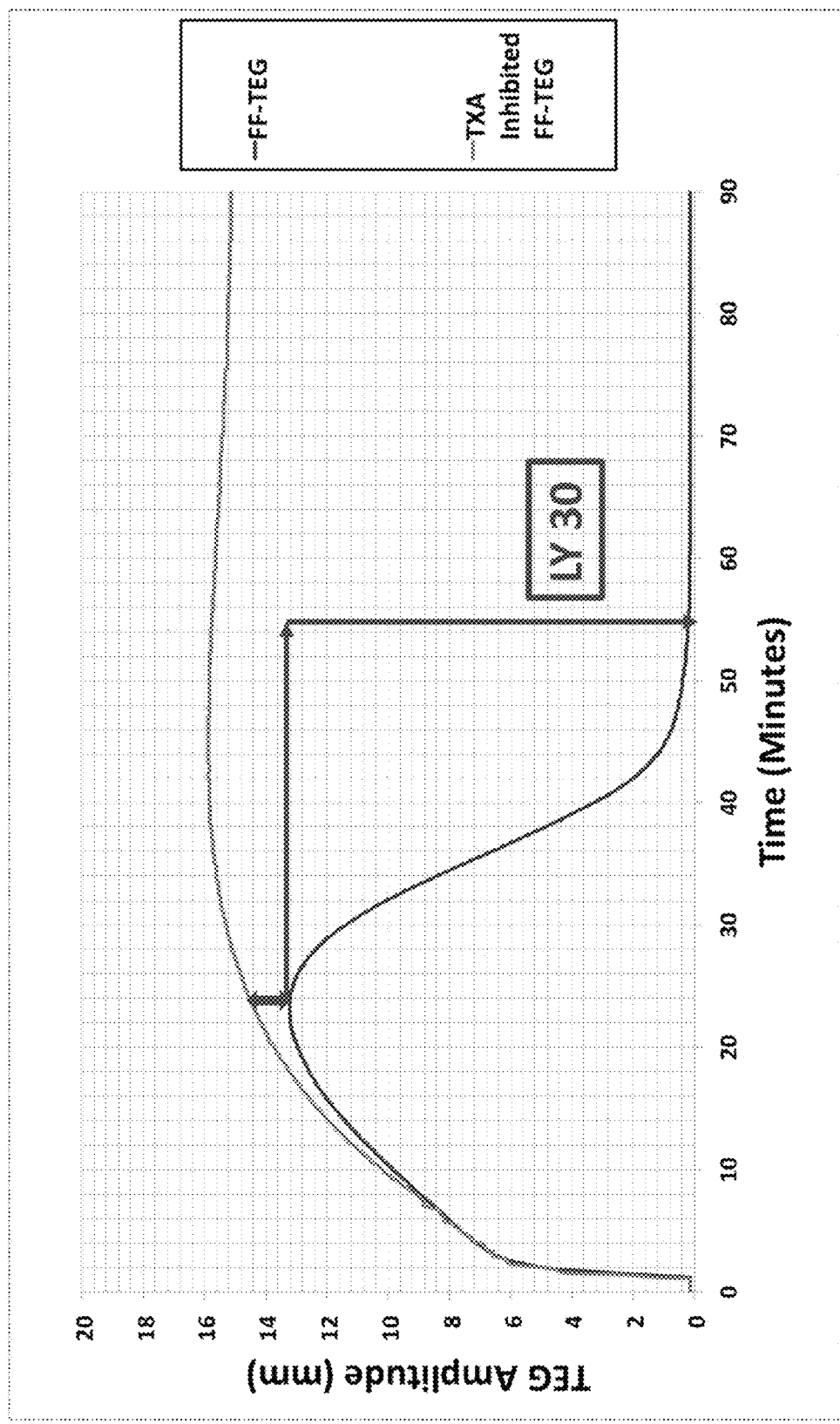
FIG. 6 is a schematic diagram showing the differences in TEG tracings of a blood sample treated with tranexamic acid (a non-limiting fibrinolysis inhibitor) (top line, green) and a blood sample not treated with tranexamic acid (bottom line, blue). In the experiment whose results are shown in this figure, both blood samples were treated with a non-limiting platelet function inhibitor. The LY30 value is superimposed over the TEG tracing of the blood sample not treated with tranexamic acid.

In some embodiments, the ΔVA is obtained at the MA of the sample not treated with the inhibitor of fibrinolysis. For convenience, this coagulation characteristic is referred to as the ΔVA@MA. The ΔVA@MA is depicted in FIG. 6 as a two-headed arrow between the two tracings at 24 minutes.

Note that any of the parameters (e.g., ΔVA, ΔLY30) that are used as the coagulation characteristic can be obtained by standard methods. Furthermore, the parameters can be obtained using a computer, a calculator, or a computer program or software.

Of course, the second derivative of the velocities can also be obtained, and compared between the sample not treated with the antifribrinolytic agent and the sample treated with the fibrinolytic agent. Indeed, the parameter used as the coagulation characteristic will impact the sensitivity of the methods; however, the method should not be limited to any one particular parameter as a coagulation characteristic. Indeed, in a trauma situation, the routinely skilled physician may simply perform a viscoelastic assay (e.g., a TEG assay) on blood samples (e.g., platelet-deleted blood samples) from the patient, one without the antifibrinolytic agent and one with the antifibrinolytic agent) in real time, and once the two tracings begin to diverge (e.g., as early as two minutes after the start of the assay), the physician may choose to treat the patient with the antifibrinolytic agent at that very moment. Hence, the speed in detecting fibrinolysis or hyperfibrinolysis in a patient is clinically relevant, particularly in the case of trauma patients where life and death outcomes can be decided within a matter of minutes.

The methods described herein thus compare a coagulation characteristic in a blood sample treated with the inhibitor of fibrinolysis and that same coagulation characteristic in a blood sample not treated with the inhibitor of fibrinolysis. In a patient with normal blood, the selected coagulation characteristic in the blood sample treated with the inhibitor of fibrinolysis and that not treated with the inhibitor of fibrinolysis will be the same or will be very significantly similar. However, in a patient having fibrinolysis or hyperfibrinolysis, the selected coagulation characteristic in the blood sample treated with the inhibitor of fibrinolysis and that not treated with the inhibitor of fibrinolysis will differ. In some embodiments, in a patient with fibrinolysis or hyperfibrinolysis, the difference between the coagulation characteristic of the blood sample treated with the inhibitor of fibrinolysis and the blood sample not treated with the inhibitor of fibrinolysis will be at least a 1% difference, or at least a 1.5% difference, or at least a 2% difference, or at least a 2.5% difference, or at least a 3% difference, or at least a 3.5% difference, or at least a 4% difference, or at least a 4.5% difference, or at least a 5% difference, or at least a 10% difference. As the skilled artisan will understand, the amount of different will depend, of course, upon the parameter being used as the coagulation characteristic.

The invention stems, in part, from an attempt to reduce the amount of time required to detect fibrinolysis and hyperfibrinolysis, by an antifibrinolytic agent (i.e., an inhibitor of fibrinolysis) is added to the blood sample being tested. Prior to the discovery described in this disclosure, the earliest a patient could be identified as having fibrinolysis or hyperfibrinolysis using a TEG device (e.g., commercially available from Haemonetics, Corp., Braintree, Mass., USA) was once the LY30 percentage was available. Even under the most rapid circumstances, the LY30 percentage was available no earlier than 43 minutes from the start of the viscoelastic assay, assuming a reaction time of 4 minutes, a K time of 0 minutes, achieve of the MA at 9 minutes, and 30 minutes for the LY30 analysis. Typically, the LY30 percentage is not available until at least 50 minutes after the start of the viscoelastic assay. By skipping the LY30 time constraints, in some embodiments, the methods described herein can provide results regarding the state of a patient's hemostasis at least 30 minutes earlier than the LY30 percentage could be obtained for that same patient, and in some embodiments even faster than 30 minutes earlier than the LY30 percentage could be obtained.

It should be noted that when the "same patient" is referred to, this means the same patient at the same time. Hence, a patient who is perfectly healthy individual is not the same patient (for the purposes of this definition) as that same healthy individual who has just been severely injured. Obviously, the perfectly healthy uninjured individual may not have an LY30 percentage at all.

In some embodiments, the time point at which the coagulation characteristic is obtained is less than 30 minutes after the start of the viscoelastic assay. In some embodiments, the time point at which the coagulation characteristic is obtained is less than 20 minutes after the start of the viscoelastic assay, or is less than 15 minutes after the start of the viscoelastic assay, or is less than 10 minutes after the start of the viscoelastic assay, or less than 5 minutes after the start of the viscoelastic assay. In some embodiments, the time point at which the coagulation characteristic is obtained is at the time of maximum amplitude of the blood sample not treated with the inhibitor of fibrinolysis. In some embodiments, the time point at which the coagulation characteristic is obtained is at the time of maximum clot firmness of the blood sample not treated with the inhibitor of fibrinolysis. In some embodiments, the time point at which the coagulation characteristic is obtained is at the time that clot firmness reaches 20 mm in the blood sample not treated with the inhibitor of fibrinolysis In some embodiments, the antifibrinolytic agent is a plasminogen inhibitor. In some embodiments, the plasminogen inhibitor is tranexamic acid (TXA).

In some embodiments, the antifibrinolytic agent is aminocaproic acid (also known as Amicar, ε-aminocaproic acid, or 6-aminohexanoic acid). In some embodiments, the antifibrinolytic agent is aprotinin.

Inhibitors of fibrinolysis (including those listed above) are well known and can be used at known concentrations. In various embodiments, the anti-fibrinolytic agent is administered to a blood sample (e.g., a blood sample with reduced platelet function) at a concentration of between about 2.5 ug/ml to about 250 ug/ml. For those inhibitors of fibrinolysis that used therapeutically in human patients, dosages are well known and may be based on individual characteristics of the patient (e.g., state of overall health, weight, and age).

In some embodiments, the inhibitor of fibrinolysis is added to the container after the blood sample (e.g., having reduced platelet function) is added to the container.

In some embodiments, when blood being tested is placed in a container (e.g., a cup or a cuvette), the antifibrinolytic agent is in the container prior to addition of the blood sample.

In some embodiments, the antifibrinolytic agent coats the interior of the container such that it is in contact with the blood sample once the blood sample is placed into the container.

During haemostasis, platelets are also involved. Produced by megakaryocytes in the bone marrow, these small cytoplasmic vesicles, about 1 um in diameter, are full of active biological agents. Just as the enzymes of the coagulation cascade need to be activated to form a fibrin clot, four agents—adenosine diphosphate (ADP), epinephrine, thrombin, and collagen—activate platelets. An adhesive protein called glycoprotein IIb-IIIa (Gp IIb-IIIa) mediates platelet aggregation. The procoagulant factor, fibrinogen, attaches to this receptor, linking the platelets to each other. The bridging, which is linked by fibrinogen, represents the main source of aggregation. Surgery or trauma exposes the procoagulant factors to the tissue factor, triggering the coagulation cascade. Besides transforming fibrinogen into fibrin, a polymer that strengthens clots, the coagulation cascade produces large amounts of thrombin, the main activator of platelets.

In some embodiments, the contribution of platelets to a patient's clot formation and strength may be removed or reduced, thereby allowing the determination of hyperfibrinolysis or fibrinolysis to be based upon only the fibrin content of the clot, and the contribution of fibrinogen.

Thus in some embodiments, the blood sample is a blood sample that has reduced platelet function. For example, the blood sample may be contacted with a platelet function inhibitor to reduce the function of the platelets in the blood sample. The blood sample may also be physically manipulated (e.g., subjected to centrifugation) to reduce the number of platelets in the blood sample by physical removal of the platelets from the blood sample.

As mentioned above, fibrinogen and platelets both contribute to clot integrity. In some of the methods described herein, fibrinolysis may be detected in a blood sample where platelet function has been reduced (for example by treating the sample with a platelet inhibitor such as cytochalasin D). If fibrinolysis in the platelet function-reduced sample is prevented with the addition of an anti-fibrinolytic agent (e.g., tranexamic acid), the fibrinolysis is likely not due to platelet function but, rather, to fibrin and other factors in the coagulation cascade. Therefore, the patient from whom the sample was obtained (and who is prone to develop, or is currently undergoing fibrinolysis or hyperfibrinolysis) will likely respond to treatment with an anti-fibrolytic agent. Thus, in some embodiments, the blood sample being tested has reduced platelet function as compared to normal whole blood.

Note that by "reduced platelet function" does not mean that the blood sample does not have any platelet function at all. Rather, the blood sample with reduced platelet function simply has reduced platelet function as opposed to normal whole blood. For example, a blood sample with reduced platelet function includes a blood sample that has a platelet function that is at least 25% less, or at least 50% less, or at least 75% less, or at least 90% less platelet function than whole blood. Platelet function includes, without limitation, the contribution to hemostasis. Reduced platelet function can thus be assessed by a reduction in the aggregation of platelets to one another during blood clotting (e.g., in the presence of Kaolin and calcium).

In some embodiments, the blood sample is physically manipulated to reduce the number of platelets in the blood sample. For example, whole blood can be centrifuged to remove some or most of the platelets. In one very simple procedure, 1.5 ul of blood can be centrifuged in a 2.0 ml microcentrifuge tube at 1000 rpm for 10 minutes. The platelet-rich plasma will float on the top of the blood in the supernatant. This supernatant can be removed (e.g., by aspiration) leaving the platelet reduced whole blood at the bottom of the tube. As less than 500 ul of blood is needed to perform the viscoelastic analyses described below, this is a very rapid method to quickly reduce the number of platelets in the blood.

In another method, platelet reduced whole blood can be obtained by contacting whole blood with platelet-specific antibodies attached to a solid surface. The platelets will selectively bind to the solid surface, and the platelet reduced whole blood can be obtained. For example, antibodies that specifically bind to the glycoprotein receptor (which is expressed on platelets but not on red blood cells) can be coupled to magnetic beads (e.g., the Dynabeads commercially available from Life Technologies, Carlsbad, Calif., USA). Whole blood can be contacted with the antibody-coated magnetic beads and, after the platelets are allowed to be bound by the antibodies, a magnetic applies. The magnet will attract the beads (and thereby will attract the platelets), and the remaining blood that has a reduced platelet content (and thus a reduced platelet function) will not be bound to the magnetic and can thus be collected.

In some embodiments, platelet function is reduced by contacting the blood sample with a platelet function inhibitor. One non-limiting platelet function inhibitor is abciximab (also known as c7E3 Fab). Abciximab is a glycoprotein IIb/IIIa receptor antagonist and inhibits platelet aggregation. Additional non-limiting platelet function inhibitors include adenosine diphosphate (ADP) receptor inhibitors (e.g., clopidogrel, prasugrel, ticagrelor, ticlopidine), phosphodiesterase inhibitors (e.g., cilostazol) glycoprotein IIb/IIIa receptor inhibitors (e.g., abciximab, eptifibatide, and tirofiban), adenosine reuptake inhibitors (e.g., dipyridamole) and thromboxane inhibitors, including thromboxane synthase inhibitors and thromboxane receptor antagonists (e.g., tertroban). Any of these platelet function inhibitors (or combinations thereof) can be used in the methods described herein.

Platelet function inhibitors (including those listed above and combinations thereof) are well known and can be used at known concentrations to reduce platelet function in whole blood. In various embodiments, the platelet function inhibitor is administered to a blood sample (e.g., a whole blood sample) at a concentration of between about 2.5 ug/ml to about 250 ug/ml.

In some embodiments of the methods described herein, once a whole blood sample is collected from the patient, the blood may be treated in such a way to reduce platelet function in the sample (e.g., by physical manipulation or by contact with a platelet function inhibitor). For example, the whole blood can be placed into a single container already containing an inhibitor of platelet function. Or, an inhibitor of platelet function can be added to the container containing whole blood. Or, the whole blood can be platelet depleted (e.g., by physically removing platelets from the blood). Following reduction in platelet function, the blood sample can then be separated into the two viscoelastic assay test groups, with the first test being performed in the absence of the fibrinolysis agent and the second test being performed in the presence of the antifibrinolysis agent.

Of course in some embodiments, the platelet function of the samples is reduced at the same time that the antifibrinolysis agent is added to the second test group. Thus, in some embodiments, when blood sample being tested is placed in a container (e.g., a cup or a cuvette), the platelet function inhibitor is in the container prior to addition of the blood sample. In some embodiments, the platelet function inhibitor coats the interior of the container such that it is in contact with the blood sample once the blood sample is placed into the container.

A functional fibrinogen assay using the thromboelastography (TEG) methodology is commercially available from Haemonetics, Corp. (Braintree, Mass., USA). This assay includes a platelet inhibitor and thus removes the contribution of platelets from the measurement of fibrinolysis. The use of this functional fibrinogen assay has described (see Harr et al., *Shock* 39(1): 45-49, 2013).

As described below, to detect fibrinolysis or hyperfibrinolysis at a very early stage, a functional fibrinogen (FF) assay (i.e., a TEG assay removing the contribution of platelets to the haemostasis process) is modified by performing the FF assay in the presence or absence of an anti-fibrinolytic agent. Although normal blood will show identical TEG and TEM tracings in both the presence and absence of an anti-fibrinolytic agent, blood from a patient with fibrinolysis or hyperfibrinolysis will show a difference between the tracings in the presence of the anti-fibrinolytic agent as compared to the tracings in the absence of an anti-fibrinolytic agent.

In another aspect, the invention provides a method for identifying an inhibitor of fibrinolysis that a patient will be responsive to. The method includes subjecting a first portion of the blood sample comprising reduced platelet function to viscoelastic analysis in the absence of an inhibitor of fibrinolysis to obtain the coagulation characteristic of the first portion at the time point; subjecting a second portion of a blood sample comprising reduced platelet function to viscoelastic analysis in the presence of first inhibitor of fibrinolysis to obtain a coagulation characteristic of the second portion at a time point; subjecting a third portion of a blood sample comprising reduced platelet function to viscoelastic analysis in the presence of first inhibitor of fibrinolysis to obtain a coagulation characteristic of the third portion at a time point; and comparing a first difference between the coagulation characteristic of the first portion and the coagulation characteristic of the second portion in the presence of the first inhibitor, and a second difference between the coagulation characteristic of the first portion and the coagulation characteristic of the third portion in the presence of the second inhibitor, wherein the patient will have beneficial result from treatment with the first inhibitor if the first difference is greater than the second difference, and the patient will have a beneficial result from treatment with the second inhibitor if the second inhibitor is greater than the first inhibitor.

Of course, the method can include a third inhibitor of fibrinolysis, etc. In some embodiments, each of the first inhibitor and the second inhibitor of fibrinolysis is selected from the group consisting of (ε-aminocaproic acid), tranexamic acid, and aprotinin, wherein the first inhibitor and the second inhibitor are not the same. Inhibitors of fibrinolysis can be used, for example, within a range of between about 2.5 ug/ml to about 250 ug/ml.

In another aspect, the invention provides a container adapted for detecting the hemostasis status of a blood sample using viscoelastic analysis comprising an interior having a coating comprising an inhibitor of platelet function. The platelet function inhibitor may be a glycoprotein IIb/IIIa receptor inhibitor (e.g., abciximab, eptifibatide, or tirofiban), or may be an adenosine diphosphate (ADP) receptor inhibitor, adenosine reuptake inhibitor, or a thromboxane inhibitor, or may be cytochalasin D. In some embodiments, the inhibitor of platelet function is a combination of different inhibitors (e.g., a combination of abciximab, eptifibatide, tirofiban, an adenosine diphosphate (ADP) receptor inhibitor, an adenosine reuptake inhibitor, a thromboxane inhibitor and/or cytochalasin D.

In another aspect, the invention provides a container adapted for detecting hyperfibrinolysis or fibrinolysis in a blood sample using viscoelastic analysis comprising an interior having a coating comprises an inhibitor of fibrinolysis. In some embodiments, the coating on the interior of the container further comprises an inhibitor of platelet function.

In some embodiments, the inhibitor of fibrinolysis in the coating of the container is tranexamic acid. In some embodiments, the inhibitor of fibrinolysis aminocaproic acid (ε-aminocaproic acid), tranexamic acid, or aprotinin. In some embodiments, the inhibitor of fibrinolysis is formulated with sugar and/or sodium azide in the coating.

In some embodiments, the container is used in a viscoelastic analysis performed using a TEG thromboelastography analyzer system or in a ROTEM thromboelastometry analyzer system.

In some embodiments, the coating of the container further comprises an inhibitor of platelet function. The platelet function inhibitor may be a glycoprotein IIb/IIIa receptor inhibitor (e.g., abciximab, eptifibatide, or tirofiban), or may be an adenosine diphosphate (ADP) receptor inhibitor, adenosine reuptake inhibitor, or a thromboxane inhibitor, or may be cytochalasin D.

The following examples are provided which are meant to illustrate but not limit the invention described herein.

Example 1: A Functional Fibrinogen TEG Assay with Tranexamic Acid (TXA)

The methods of Harr et al., supra, are generally followed. Briefly, citrated whole blood samples are obtained from trauma patients. Venipuncture is performed with a 21-gauge needle in an antecubital vein, and blood is collected into evacuated containers containing 3.2% citrate (e.g., a 3.5 mL plastic Vacutainers® containing 3.2% citrate).

The Functional Fibrinogen assay is purchased from Haemonetics Corp. (Niles, Ill., USA and Braintree, Mass., USA), and performed on the TEG® 5000 device according to manufacturer's instructions.

To perform the Functional Fibrinogen (FF) assay, 0.5 mL of citrated blood is added to the designated FF-vial containing a mixture of tissue factor (a coagulation activator) and the abciximab (a monoclonal GPIIb/IIIa receptor antagonist; sometimes referred to as the FF reagent), and the blood sample is gently mixed. A 340 uL aliquot is transferred from the FF-vial to a 37° C. TEG cup preloaded with 20 μL 0.2 mol/L of CaCl2. The FF-assay measures the coagulation parameters of a platelet-free clot. A second 340 uL aliquot is transferred from the FF-vial to a 37° C. TEG cup preloaded with 20 μL 0.2 mol/L of CaCl2, where the second TEG cup is coated with TXA according to the method described in Example 2.

The two portions of the blood sample (i.e., the FF without TXA and the FF plus TXA) are analyzed simultaneously on a TEG 5000 device. If the blood sample is normal, the two tracings will be nearly identical and will form one line (or two very close lines) when overlaid with one another.

Figure 5:
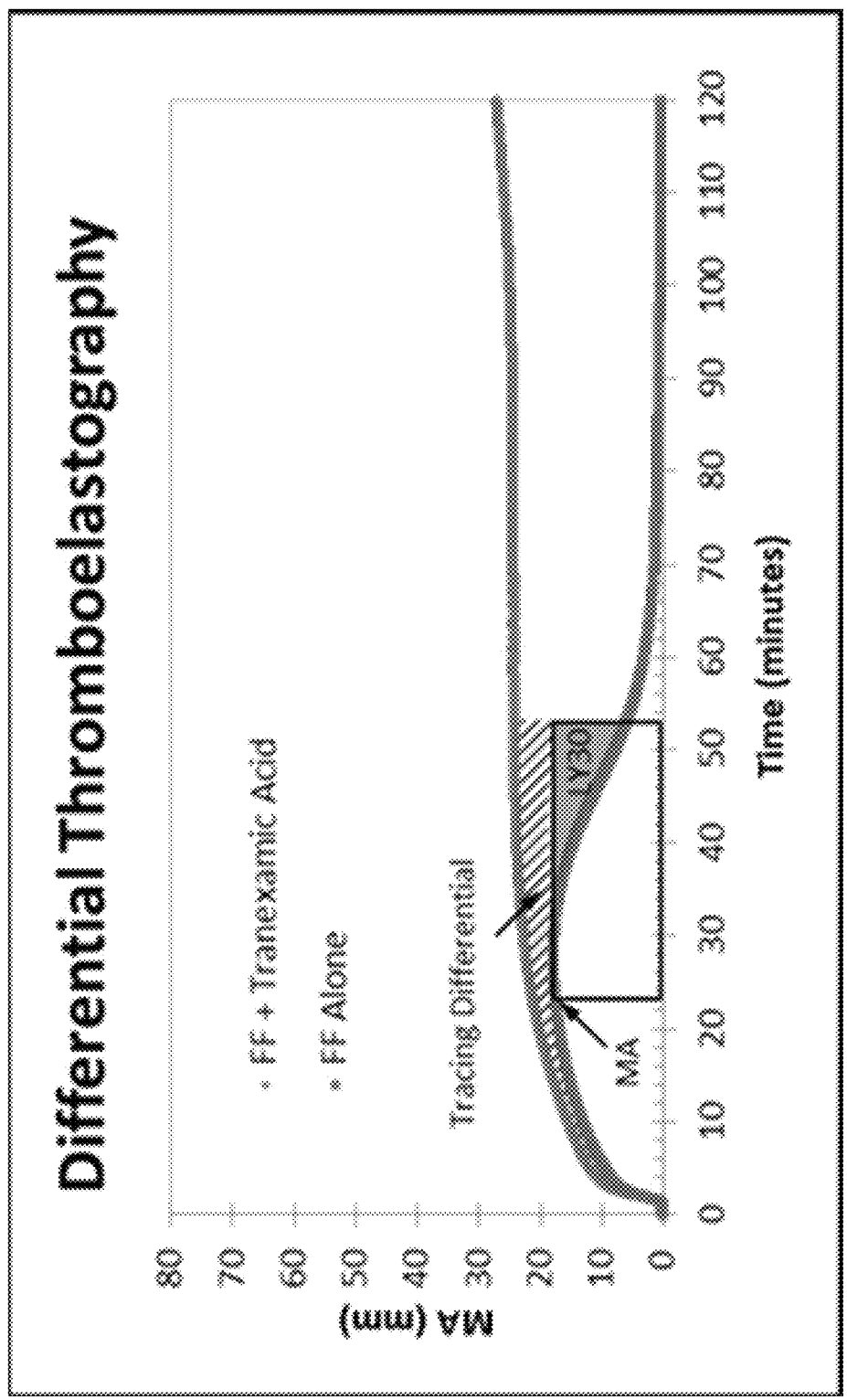
FIG. 5 is a schematic diagram showing the differences in TEG tracings of a blood sample treated with tranexamic acid (a non-limiting fibrinolysis inhibitor) (top line, blue) and a blood sample not treated with tranexamic acid (bottom line, red). In the experiment whose results are shown in this figure, both blood samples were treated with a non-limiting platelet function inhibitor.

However, if the blood sample is taken from a patient who has fibrinolysis or hyperfibrinolysis, the TXA-treated portion of the blood sample will provide a TEG tracing that is markedly different than the TEG tracing of the portion of the blood same that is not treated with TXA. FIGS. 5 and 6 show representative results from these studies. As shown, the TXA-treated portion of the blood sample will have a higher amplitude, faster growing TEG tracing. The divergence of these TEG tracing occurs almost immediately (e.g., at 2 minutes after the assay starts), and is clearly different at between about 15 to about 35 minutes after the assay is started (e.g., about 15 to about 35 minutes after the pin is inserted into the cup). The difference is markedly clear at the time of the MA of the TEG tracing of the FF alone (i.e., the FF without TXA)-treated blood sample.

From the data obtained in FIGS. 5 and 6 (or similar results), a new parameter, namely ΔV@MA has been developed. ΔV@MA is the differential in velocity of the two channels (i.e., blood without TXA and blood in the presence of TXA) at the MA time of the blood sample not treated with TXA. Thus, ΔV@MA can be calculated by simply subtracting the TEG velocity of the sample not treated with TXA (the bottom line in FIGS. 6 and 7) from the TEG velocity of the sample treated with TXA (the top lines in FIGS. 6 and 7).

Figure 7:
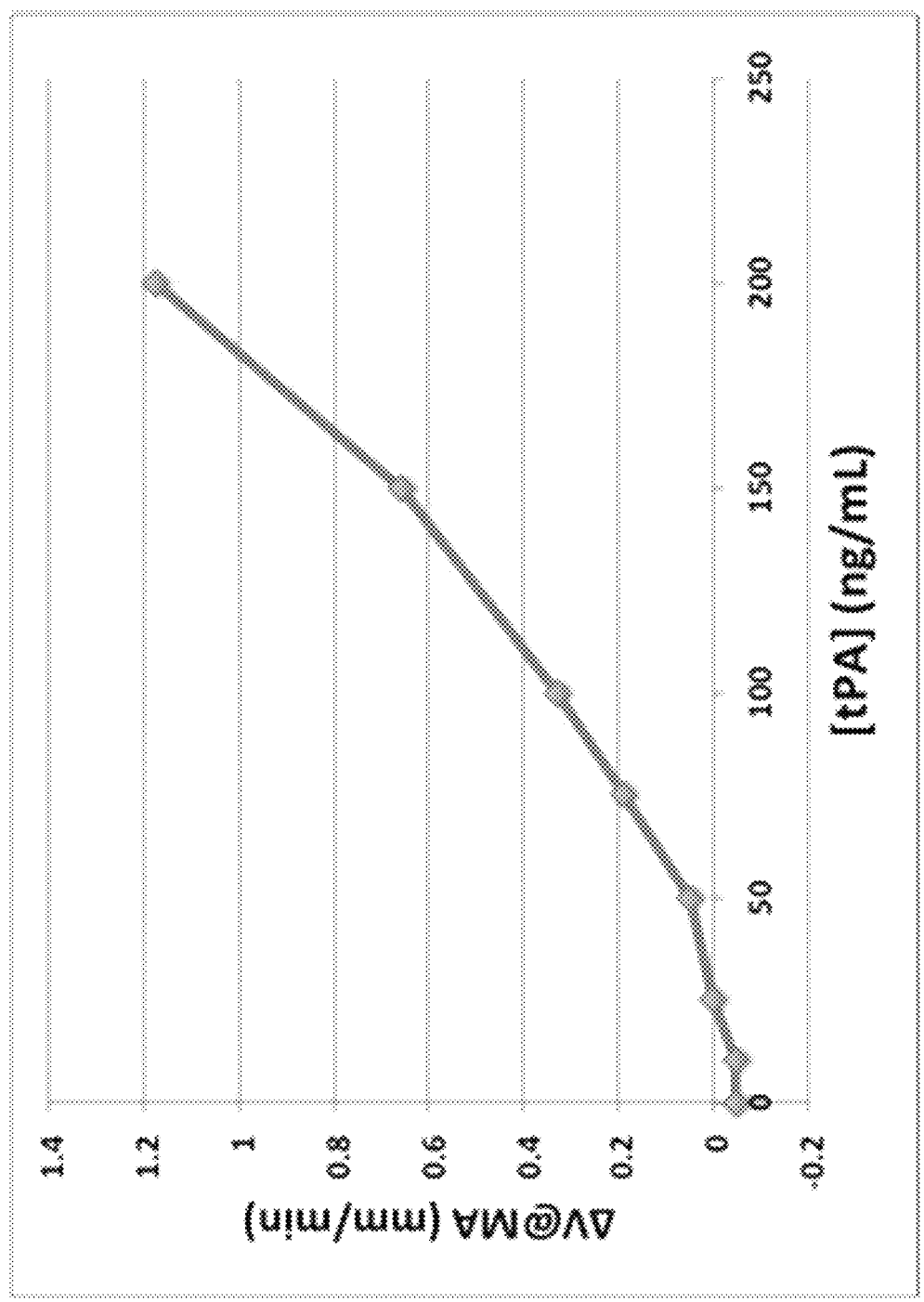
FIG. 7 is a line graph plotting ΔV@MA against increasing concentration of t-PA.

To determine if this new parameter, namely $\Delta V@MA$ is indicative of fibrinolysis, first a standard titration curve was created. As discussed above, t-PA (tissue plasminogen activator) can convert inactive plasminogen to active plasmin, which can then break down fibrin and thus induce fibrinolysis. Whole blood from a healthy person was collected spiked with increasing amounts oft-PA, and the blood sample divided equally, with TXA being added to one portion but not to the other portion. The two portions (i.e., two samples) were subjected to analysis on a TEG 5000 device, and the $\Delta V@MA$ (subtracting the TEG velocity of the sample not treated with TXA from the sample treated with TXA at the MA of the sample not treated with TXA). FIG. 7 is a line graph showing $\Delta V@MA$ plotted against the concentration of tPA (at ng/ml), revealing a standard titration curve.

The next question was whether this new parameter, $\Delta V@MA$ correlated with LY30 which, as discussed above, is the art-known method for detecting fibrinolysis. To do this, a calculation of the $\Delta LY30$ was performed, again calculating the difference between the LY30 number of a TXA-treated sample and an LY30 number of a sample not treated with TXA. The LY30 of a sample not treated with TXA is straight forward. For example, referring to FIG. 6, the LY30 of the sample not treated with TXA is approximately 50% (where the MA is approximately 24 minutes into the assay, and the LY30 is calculated 30 minutes later. For the TXA treated sample, the LY30 is very small, being approximately 0.1% (calculating the LY30 based on the amplitude of the TXA-treated sample at 74 minutes). As discussed above, an LY30 as low as 3% may be clinically relevant. Therefore, a $\Delta LY30$ of as low as 3% may also be clinically relevant. The LY30 of roughly 50% in the untreated sample in this example represents very severe hyperfibrinolysis.

Figure 8:
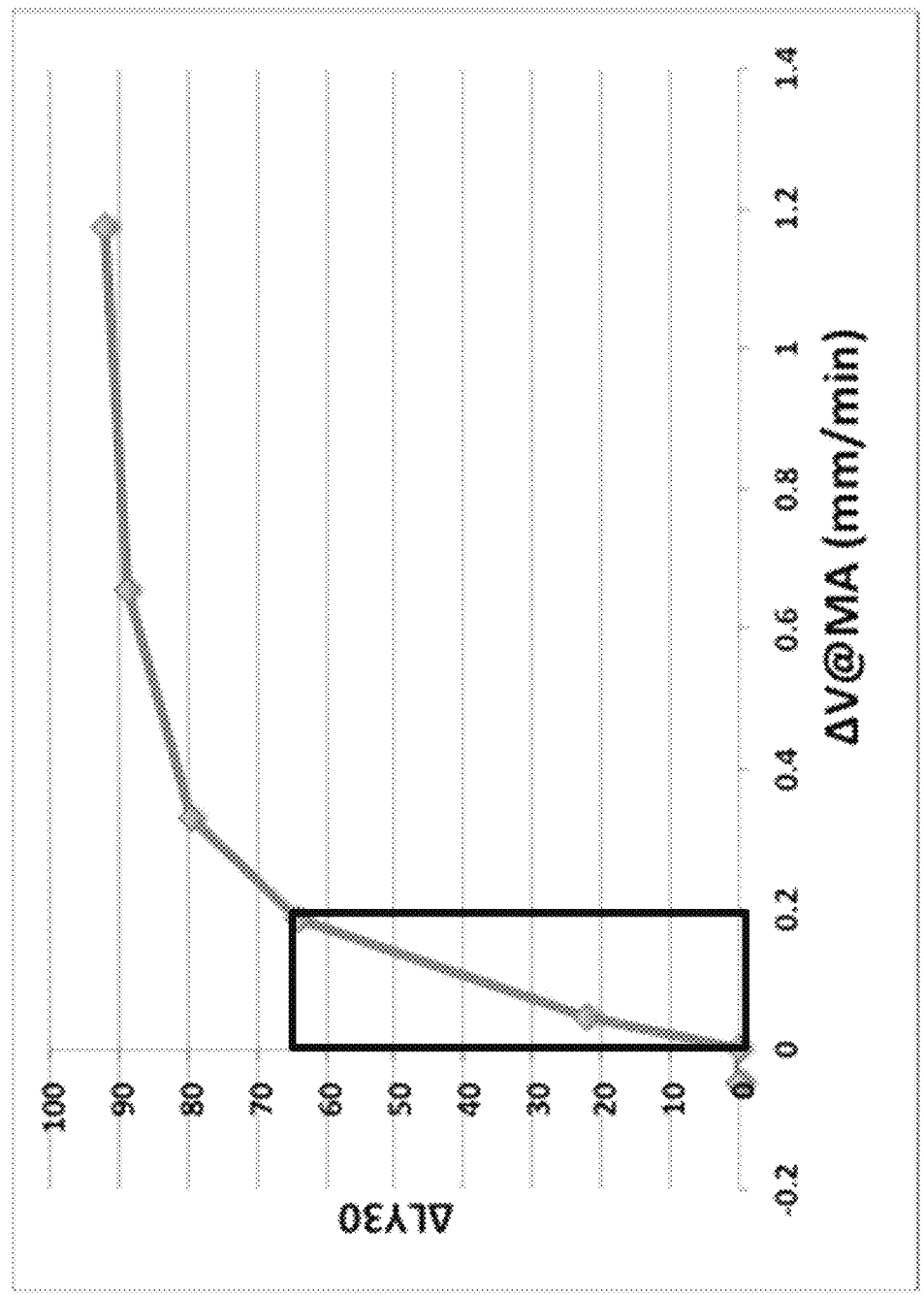
FIG. 8 is a line graph plotting ΔV@MA against ΔLY30.

As shown in FIG. 8, within the clinically relevant range of LY30, the $\Delta V@MA$ versus $\Delta LY30$ curve is linear. Therefore, the new $\Delta V@MA$ parameter, which is calculated at the time of the MA of the sample not treated with TXA, and is, by definition, obtained 30 minutes faster than the $\Delta LY30$ parameter, is a valid metric of fibrinolysis, but is available to the clinician much faster than the LY30. Such a reduction in the time needed to detect fibrinolysis and hyperfibrinolysis is critically important for the outcome of trauma patients.

Note that as discussed above, the $\Delta V$ need not be obtained at the MA of the sample not treated with TXA. Rather, the $\Delta V$ can be obtained at any time the inhibitor of fibrinolysis-treated sample and the sample not treated with inhibitor of fibrinolysis start showing diverging TEG tracings.

Example 2: Production of Containers Coated with TXA (Tranexamic Acid)

Preparation of the TXA-Coated TEG Cup.

Prepare 15 mL stock using: 1.282 mLs 11.7% trehalose; 0.03 mLs 10% NaN3; 0.9 mLs Cyklokapron (commercial preparation of tranexamic acid, 100 mg/mL TXA in H2O); and 12.788 mL deionized H2O.

30 uL of this solution is dispensed into a TEG cup, for a final TXA strength of 180 ug/cup. The cups are air-dried overnight, and packaged 20 cups (and pins) per box, with a desiccant pack. Each box is packaged in a sealed Ziploc bag.

The final matrix for the drug solution (before drying) is 1% trehalose and 0.02% NaN3. Note that the drying process may be performed in a lyophilizer, in which case the drying process may be referred to as lyophilization.

Using this method described in Example 2, the amount of TXA in each cup can be standardized, and the TXA coated cups can be easily stored for later use.

Example 3: Production of Containers Coated with Either an Anti-Fibrinolytic Agent and an Inhibitor of Platelet Function or with Only an Inhibitor of Platelet Function For the cups with both TXA and the platelet inhibitor, a solution containing sodium azide, trehalose, tranexamic acid (TXA), and cytochalasin D is prepared and used to coat the interior of TEG cups. As described in Example 2, the solution is applied, and then the cups allowed to dry. The final concentration of TXA in each cup is 180 ug/cup. The final concentration of cytochalasin D in each cup is within a range of between about 2.5 ug/ml to about 250 ug/ml.

For the cups with only platelet inhibitor, a solution containing sodium azide, trehalose, and cytochalasin D is prepared and used to coat the interior of TEG cups. The solution is applied to the cups, and then the cups allowed to dry. The final concentration of cytochalasin D in each cup is within a range of between about 2.5 ug/ml to about 250 ug/ml.

Example 4: A TEG Assay with Tranexamic Acid (TXA)

For these studies, the protocol in Example 1 is followed, but the blood is not citrated and no activator is added to the blood.

Briefly, whole blood is collected from a patient brought in for surgery. The blood sample taken is immediately divided into two portions of 360 uL each and each portion is placed into TEG cups. The first portion is added to a TEG cup coated a coating comprising the FF reagent (a monoclonal GPIIb/IIIa receptor antagonist) and 200 ug tranexamic acid (TXA). The second portion is added to a TEG cup coated with a coating comprising 200 ug TXA.

The two portions of the blood sample (i.e., the FF-no TXA and the FF plus TXA) are analyzed simultaneously on a TEG 5000 device. If the blood sample is normal, the two tracings will be identical and will form one line when overlaid with one another.

However, at the moment the two tracings start to diverge (e.g., as early as two minutes after the start of the analysis), a small dosage of the anti-fibrinolysis agent used in the TEG assay (in this case, tranexamic acid) is prepared for administration to the patient. The dosage may be increased or not depending upon how much the two tracings diverge. For example, if the two tracings diverge extremely at, e.g., 20 minutes after the start of the analysis, the patient likely has hyperfibrinolysis. At this point, the dosage of the anti-fibrinolysis agent (e.g., tranexamic acid or aprotinin) may be increased to improve the chances of a favorable outcome for the patient during and following the surgical procedure.

Example 5: Comparison of the Citrated Kaolin (CK) TEG to the Methods Described Herein The method described herein, comparing a coagulation characteristic of the patient's blood sample that is not treated with an antifibrinolytic agent to that coagulation characteristic of the patient's blood sample that is treated with an antifibrinolytic agent is a superior and more sensitive test than the citrated kaolin test.

To prove this concept, blood was taken from 15 donors and separated into two groups—the Citrated Kaolin group and the FF (Functional Fibrinogen) group.

Figure 9:
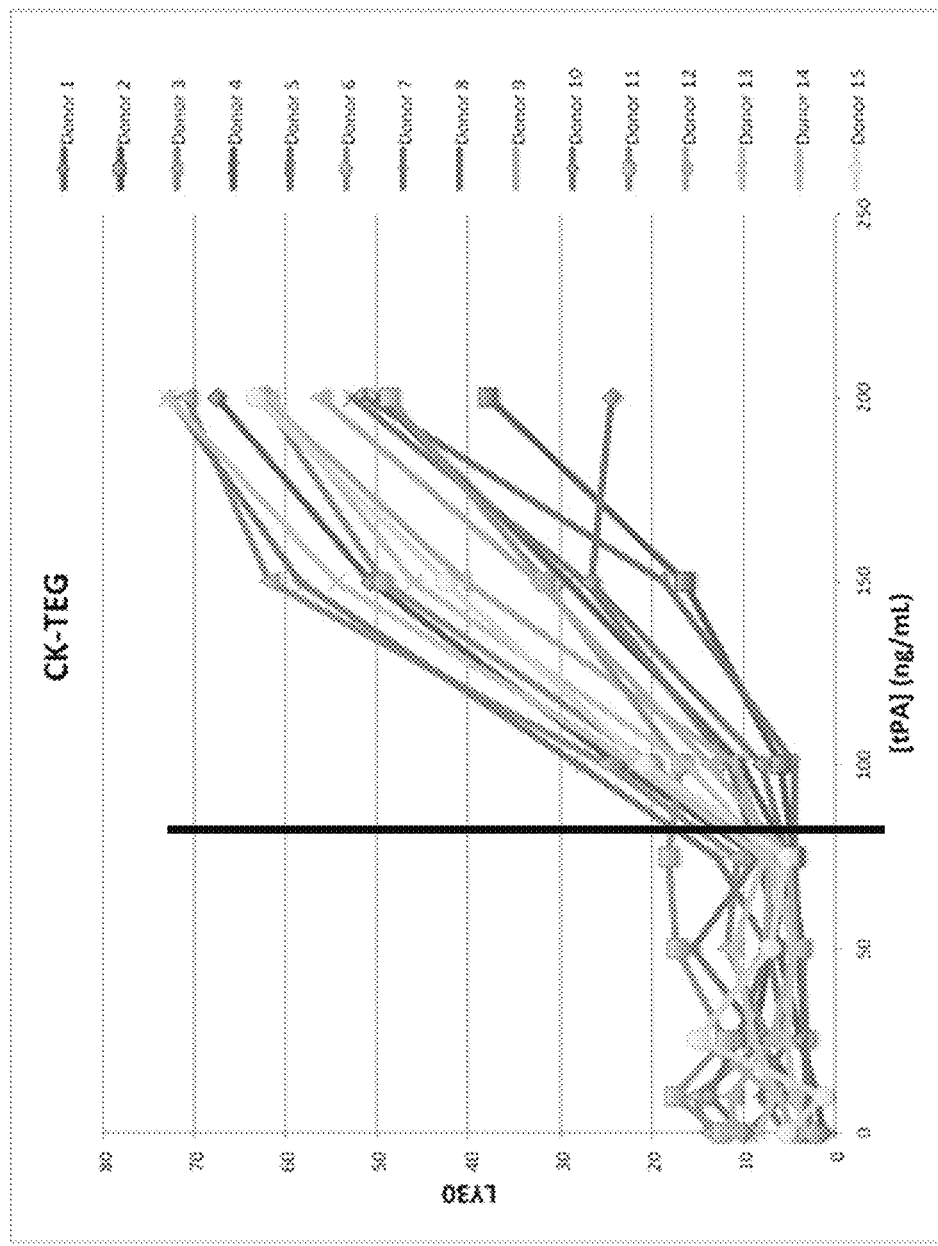
FIG. 9 is a line graph plotting LY30 against increasing concentration of t-PA from blood samples of fifteen healthy donors using the citrated kaolin TEG assay.

For the Citrated Kaolin group, citrated blood from each of the donors (e.g., whole blood collected into a tube containing sodium citrate (thereby creating a ratio blood to citrate of approximately 9:1) is collected. For eight different tPA concentrations, 0.5 ml of the blood was gently mixed with Kaolin (a coagulation activator) and increasing concentrations oft-PA to induce fibrinolysis. Aliquots were transferred to 37° C. TEG cups, and the samples were analyzed using the TEG 5000 device, and the LY30 calculated for each of the 15 donors at each of the tPA concentrations. The results plotting the LY30 against the t-PA concentration are shown in FIG. 9. As shown by the vertical line in FIG. 9, the lysis signal does not rise out of the baseline noise until a t-PA concentration of between about 75 ng/ml and 100 ng/ml is reached.

For the Functional Fibrinogen (FF) group, citrated blood is collected from each of the donors. For eight different t-PA concentrations, 0.5 ml of the blood was gently mixed with increasing concentrations oft-PA and the FF reagent (a GPIIb/IIIa receptor antagonist), and the blood samples were gently mixed. An aliquot was transferred to a 37° C. TEG cup preloaded with CaCl2. A second aliquot was transferred to a 37° C. TEG cup preloaded with CaCl2, where the second TEG cup is coated with TXA.

The two TEG cups for each of the fifteen donors at the eight different t-PA concentrations were analyzed on a TEG 5000 device. From these tracings, a calculation of the ΔLY30 was performed for each donor. As described above, the ΔLY30 is simply the difference between LY30 of the sample not treated with TXA (calculated using the amplitudes at the MA time point and 30 minutes from the MA time point of the untreated sample) and the LY30 of the TXA-treated sample (calculated using the amplitudes at the MA time point and 30 minutes from the MA time point of the TXA-treated sample).

Figure 10:
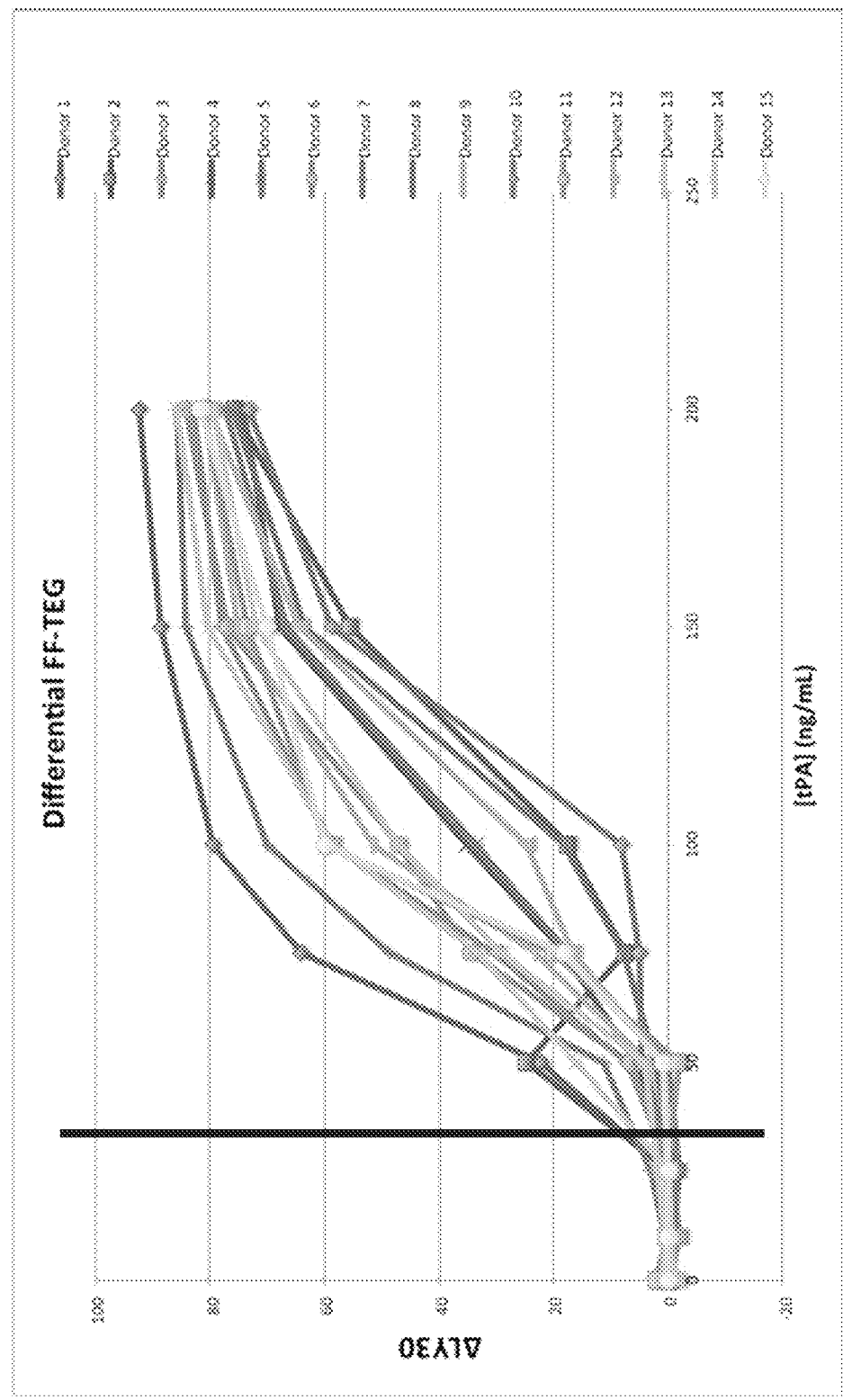
FIG. 10 is a line graph plotting the ΔLY30 against increasing concentration of t-PA from blood sample of fifteen healthy donors using one of the non-limiting methods described herein, where ΔLY30 is the difference between the LY30 of a functional fibrinogen assay and the LY30 of a functional fibrinogen assay in the presence of an inhibitor of fibrinolysis, tranexamic acid.

The results plotting the ΔLY30 against the t-PA concentration are shown in FIG. 10. As shown by the vertical line in FIG. 10, the lysis signal occurs between about 25 and 50 ng/ml t-PA. Thus, the detection threshold of the method described herein is over 2 times higher than that of the citrated Kaolin test (compare FIG. 10 to FIG. 9).

Based on these studies, the following sensitivity and specificity parameters were achieved:
Sensitivity Parameters:
  Detection threshold [tPA]: 25-50 ng/mL for ΔLY30; 75-100 ng/mL for CK-LY30
  Analytical sensitivity (slope from 75-100 ng/mL): 19.67 for ΔLY30; 8.01 for CK-LY30
  RSD of the slope (n=15): 0.57 for ΔLY30; 0.77 for CK-LY30
  Linear Correlation ($R^2$ from 0-200 ng/ml): 0.87 for ΔLY30; 0.72 CK-LY30
Specificity Parameters:
  Baseline signal (mean level below detection threshold): −0.12 for ΔLY30; 7.38 CK-LY30
  Baseline noise (SD in baseline signal): 0.95 ΔLY30; 4.18 CK-LY30

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A container adapted for detecting hyperfibrinolysis or fibrinolysis in a blood sample using viscoelastic analysis comprising an interior having a coating comprising an inhibitor of fibrinolysis and an inhibitor of platelet function,
  Wherein the coating is produced by applying a solution comprising both the inhibitor of fibrinolysis and the inhibitor of platelet function to the interior of the container and drying the solution such that it forms the coating on the interior of the container.

2. The container of claim 1, wherein the inhibitor of fibrinolysis is tranexamic acid.

3. The container of claim 1, wherein the inhibitor of fibrinolysis is selected from the group consisting of aminocaproic acid, ε-aminocaproic acid, and aprotinin.

4. The container of claim 1, wherein the viscoelastic analysis is performed using a thromboelastography analyzer system or in a thromboelastometry analyzer system.

5. The container of claim 1, wherein the inhibitor of fibrinolysis is formulated with sugar in the coating.

6. The container of claim 1, wherein the inhibitor is formulated with sodium azide in the coating.

7. The container of claim 1, wherein the inhibitor of platelet function is a glycoprotein IIb/IIIa receptor inhibitor.

8. The container of claim 7, wherein the glycoprotein IIb/IIIa receptor inhibitor is selected from the group consisting of abciximab, eptifibatide, and tirofiban.

9. The container of claim 1, wherein the inhibitor of platelet function is an adenosine diphosphate (ADP) receptor inhibitor, adenosine reuptake inhibitor, or a thromboxane inhibitor.

10. The container of claim 1, wherein the inhibitor of platelet function is cytochalasin D.

11. The container of claim 1, wherein the container is located on a cassette, wherein the cassette further comprises a second container.

* * * * *